(12) United States Patent
Wong et al.

(10) Patent No.: US 7,999,000 B2
(45) Date of Patent: Aug. 16, 2011

(54) N-(2-AMINO-PHENYL)-ACRYLAMIDES

(75) Inventors: Jason Christopher Wong, Shanghai (CN); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 108 days.

(21) Appl. No.: 12/463,452

(22) Filed: May 11, 2009

(65) Prior Publication Data
US 2009/0286848 A1 Nov. 19, 2009

(30) Foreign Application Priority Data

May 16, 2008 (EP) ..................................... 08156365

(51) Int. Cl.
*A61K 31/40* (2006.01)
*C07D 207/08* (2006.01)

(52) U.S. Cl. ........................................ 514/428; 548/568
(58) Field of Classification Search .................. None
See application file for complete search history.

(56) References Cited

U.S. PATENT DOCUMENTS

| 3,810,910 | A | 5/1974 | Meyer et al. |
| 2005/0245518 | A1 | 11/2005 | Delorme et al. |

FOREIGN PATENT DOCUMENTS

| DE | 2 062 265 | 5/1972 |
| FR | 2 167 954 | 8/1973 |
| WO | WO 01/38322 | 5/2001 |
| WO | WO 2006/115845 | 11/2006 |
| WO | WO 2007/087130 | 8/2007 |
| WO | WO 2007/100657 | 9/2007 |

OTHER PUBLICATIONS

Sausville et al. ( Cancer Reasearch, 2006, vol. 66, pp. 3351-3354).*
British Journal of Nursing 17(5): 300-305 (Mar. 13, 2008) Abstract only.*
Koyama et al., Blood, vol. 96 (2000) pp. 1490-1495.
Martin et al., Oncogene (2007) vol. 26, pp. 5450-5467.
Matsuoka et al., Biochemical Pharmacology (2007) vol. 74 pp. 465-476.
Rastogi et al., Indian J. Chem. Section B, 21B (1982) pp. 485-487.
Moll et al., Z. Chem. vol. 17 (1977) pp. 133-134.
Hassan et al., Indian J. Chem. 39B (2000) pp. 764-768.
Bastin et al., Organic Process Research & Development (2000) vol. 4 pp. 427-435.
Ansel et al., Pharmaceutical Dosage Forms and Drug Delivery Systems (1995) pp. 456-457.
Zhang et al., Mol. Cell. Bio. (2004) vol. 24 pp. 5106-5118.

* cited by examiner

*Primary Examiner* — Kamal Saeed
(74) *Attorney, Agent, or Firm* — George W. Johnston; Patricia S. Rocha-Tramaloni; David E. Wildman

(57) ABSTRACT

The present invention is directed to the compounds of formula

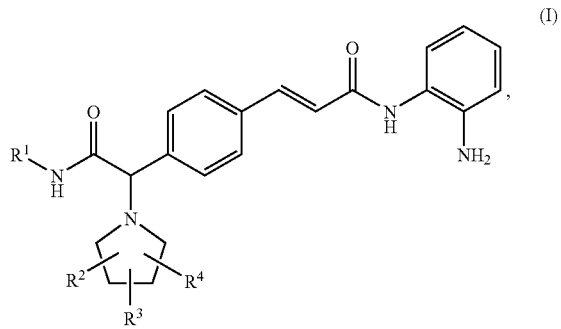

wherein $R^1$ to $R^4$ have the significances given herein, to processes for the manufacture of said compounds as well as medicaments containing said compounds. The compounds according to this invention show anti-proliferative and differentiation-inducing activity and are thus useful for the treatment of diseases such as cancer in humans or animals.

8 Claims, No Drawings

N-(2-AMINO-PHENYL)-ACRYLAMIDES

PRIORITY TO RELATED APPLICATION(S)

This application claims the benefit of European Patent Application No. 08156365.2, filed May 16, 2008, which is hereby incorporated by reference in its entirety.

BACKGROUND OF THE INVENTION

The invention relates to novel antitumor agents and pharmaceutically acceptable salts thereof, processes for the manufacture of these novel compounds and medicaments containing such compounds. The compounds of the invention have antiproliferative and differentiation-inducing activity, which results in inhibition of tumor cell proliferation, induction of apoptosis and inhibition of invasion. The invention thus also concerns the use of such compounds for the treatment of diseases such as cancer and for the manufacture of corresponding medicaments.

The compounds according to this invention are inhibitors of histone deacetylase (HDAC) and therefore show antiproliferative and differentiation-inducing activity, which results in inhibition of tumor cell proliferation, induction of apoptosis and inhibition of invasion.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Histone deacetylases (HDACs) are the key enzymatic components of multiprotein complexes responsible for deacetylation of lysine residues in histone and nonhistone protein substrates. HDACs can be subdivided into three major classes according to their sequence homology to the yeast HDACs, Rpd3, Hda1, and Sir2. The class I HDACs (HDACs 1, 2, 3, and 8), homologous to Rpd3, localize primarily in the nucleus and appear to be expressed in most tissues. The class II HDACs (HDACs 4, 5, 6, 7, 9, 10), homologous to Hda1, are able to shuttle between the nucleus and the cytoplasm depending on a variety of regulatory signals and cellular state, and have tissue-specific expression patterns. These HDACs can be further subdivided into class IIa (HDACs 4, 5, 7, 9), and class IIb (HDACs 6, 10). The class III HDACs, homologous to Sir2, are $NAD^+$-dependent deacetylases that are mechanistically distinct from the class I and II HDACs and are not inhibited by classical HDAC inhibitors such as trichostatin A, trapoxin B, or SNDX-275. The HDACs can thus be divided into three classes on the basis of sequence similarity, cellular localization tendencies, tissue expression patterns, and enzymatic mechanism.

The class I HDACs, in particular, have been closely associated with antiproliferative effects against tumor cells. For example, pharmacological inhibition of HDACs 1-3 leads to induction of the cyclin-dependent kinase inhibitor p21 and concommitant cell cycle arrest. The class IIa HDACs are known to associate with the HDAC3/SMRT/N-CoR complex and MEF2 and as such have important roles in regulating muscle cell gene expression (reviewed in *Oncogene* 2007, 26, 5450-5467) and the immune response (*Biochemical Pharmacology* 2007, 74, 465-476). Due to their specific antiproliferative function, selective inhibition of the class I HDACs may be desirable to achieve antitumor efficacy with lower toxicity.

The compounds of the present invention show enhanced potency and selectivity toward the class I HDACs over the class IIa HDACs. This potency and selectivity is evaluated by reporter gene assays that evaluate HDAC subtype activity in the context of relevant multiprotein complexes present in the cell that are typically absent in enzymatic selectivity assays. Thus, the compounds of the present invention possess in-cell selectivity that can lower toxicity associated with inhibition of the class IIa HDACs.

WO 2007/100657 describes related but structurally different o-phenylendiamine derivatives as cell differentiation inducers. The same type of compounds is also the subject of WO2007/087130. The compounds described in these applications are exclusively o-phenylene derivatives monoacylated with derivatives of benzoic acid. However there remains a need for new compounds with improved therapeutic properties, such as enhanced activity, decreased toxicity, better solubility and/or improved pharmacokinetic profile, to name only a few.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485-487; Moll, R., et al., Z. Chem. 17 (1977) 133-134; and Hassan, H., et al., Indian J. Chem. 39B (2000) 764-768.

It has been found that the compounds of the present invention are HDAC inhibitors which have anti-proliferative and differentiation-inducing activity, which results in inhibition of tumor cell proliferation, induction of apoptosis and inhibition of invasion. These compounds are therefore useful for the treatment of diseases such as cancer in humans or animals.

SUMMARY OF THE INVENTION

The present invention is directed to compounds according to formula (I),

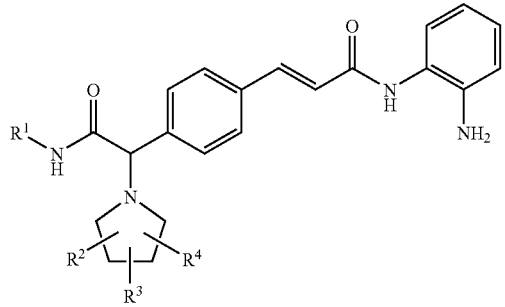

wherein:
R¹ is selected from the group consisting of: hydrogen; lower alkyl; cycloalkyl; heterocyclyl; aryl and heteroaryl; wherein said lower alkyl; cycloalkyl; heterocyclyl; aryl or heteroaryl may be unsubstituted or once or several times substituted by: halogen; lower alkyl, which is unsubstituted or once or several times substituted by halogen; lower alkoxy; cycloalkyl; cyano; —NR$^a$R$^b$; —OCF$_3$; or —S(O)$_2$-lower alkyl;

R$^a$ and R$^b$ are:
each independently lower alkyl or cycloalkyl, or
together with the nitrogen atom to which they are attached, form a 4 to 6 membered heterocyclyl;

R$^2$ and R$^3$:
are each independently selected from the group consisting of: hydrogen; halogen; lower alkyl, which is unsubstituted or once substituted by hydroxy; lower alkoxy; hydroxy; heterocyclyl; —NRR'; and

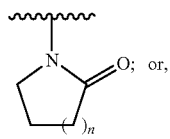

together with the carbon atoms to which they are attached, form a 4 to 6 membered cycloalkyl or a 4 to 6 membered heterocyclyl wherein one ring atom is a heteroatom;

R$^4$ is selected from the group consisting of: hydrogen; halogen; lower alkyl, which is unsubstituted or once substituted by hydroxy; lower alkoxy; hydroxy; heterocyclyl; —NRR'; and

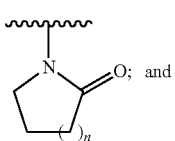

R and R' are each independently selected from the group consisting of: hydrogen; lower alkyl substituted by hydroxy; —C(O)-lower alkyl; and lower alkyl; and
n is 0, 1 or 2.

The present invention is also directed to pharmaceutically-active salts, racemic mixtures, enantiomers, optical isomers, or tautomeric forms of compounds of formula (I).

The invention is further directed to the use of the above compounds for the treatment of diseases such as cancer and for the manufacture of corresponding medicaments.

DETAILED DESCRIPTION OF THE INVENTION

The present invention is directed to compounds according to formula (I),

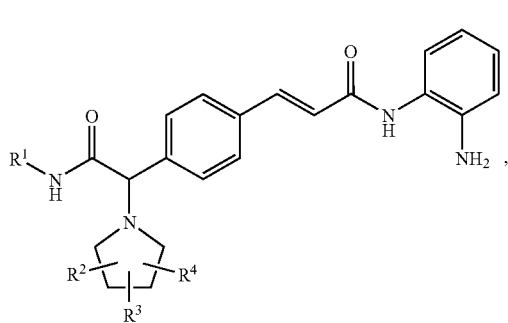

(I)

wherein:
R$^1$ is selected from the group consisting of: hydrogen; lower alkyl; cycloalkyl; heterocyclyl; aryl and heteroaryl; wherein said lower alkyl; cycloalkyl; heterocyclyl; aryl or heteroaryl may be unsubstituted or once or several times substituted by: halogen; lower alkyl, which is unsubstituted or once or several times substituted by halogen; lower alkoxy; cycloalkyl; cyano; —NR$^a$R$^b$; —OCF$_3$; or —S(O)$_2$-lower alkyl;

R$^a$ and R$^b$ are:
each independently lower alkyl or cycloalkyl, or
together with the nitrogen atom to which they are attached, form a 4 to 6 membered heterocyclyl;

R$^2$ and R$^3$:
are each independently selected from the group consisting of: hydrogen; halogen; lower alkyl, which is unsubstituted or once substituted by hydroxy; lower alkoxy; hydroxy; heterocyclyl; —NRR'; and

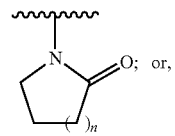

together with the carbon atoms to which they are attached, form a 4 to 6 membered cycloalkyl or a 4 to 6 membered heterocyclyl wherein one ring atom is a heteroatom;

R$^4$ is selected from the group consisting of: hydrogen; halogen; lower alkyl, which is unsubstituted or once substituted by hydroxy; lower alkoxy; hydroxy; heterocyclyl; —NRR'; and

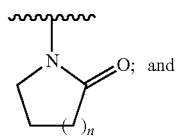

R and R' are each independently selected from the group consisting of: hydrogen; lower alkyl substituted by hydroxy; —C(O)-lower alkyl; and lower alkyl; and
n is 0, 1 or 2.

The present invention is also directed to pharmaceutically-active salts, racemic mixtures, enantiomers, optical isomers, or tautomeric forms of compounds of formula (I).

The invention is further directed to the use of the above compounds for the treatment of diseases such as cancer and for the manufacture of corresponding medicaments.

The term "lower alkyl", as used herein, denotes a saturated, linear- or branched chain hydrocarbon group containing 1 to 8, preferably 1 to 6, more preferably 1 to 4 carbonatoms, for example methyl, ethyl, propyl, isopropyl, 1-butyl, 2-butyl, tert-butyl and the like. Preferred "C$_1$-C$_8$-alkyl" groups have 1, 2 or 3 carbonatoms.

The term "lower alkoxy", as used herein, denotes a lower alkyl group that is attached to an oxygen atom; for example, methoxy, ethoxy, propoxy, isopropoxy, n-butoxy, i-butoxy, 2-butoxy, t-butoxy and the like. Preferred lower alkoxy groups are groups with 1-4 carbon atoms.

The term "cycloalkyl", as used herein, means a saturated, cyclic hydrocarbon group consisting of one or two rings which may be fused to each other or attached to each other by a single bond, and containing from 3 to 8, preferably from 3 to 6 carbon atoms. Examples of such 3 to 8 membered cycloalkyl rings include, but are not limited to, cyclopropyl, cyclobutyl, cyclopentyl, cyclohexyl, cyclooctyl, octahydroindene, bicyclo[2.2.1]heptane, bicyclohexyl and the like.

The term "heteroatom", as used herein, means an atom selected from the group consisting of: nitrogen, oxygen, and sulfur.

The term "heterocyclyl", as used herein, means a saturated mono- or bicyclic ring group having three to eight ring atoms with one to three such ring atoms being a heteroatom and the remaining ring atoms being carbon. Examples include, but are not limited to, morpholinyl, thiomorpholinyl, piperidinyl, piperazinyl, tetrahydro-pyranyl, 2-Oxa-5-aza-bicyclo[2.2.1]heptanyl, [1,4]oxathianyl, azepanyl, [1,4]diazepanyl, pyrrolidinyl, pyrazolidinyl, [1,2,3]triazolidinyl, imidazolidinyl, thiazolidinyl, azetidinyl.

The term "aryl", as used herein, means an aromatic, or partially aromatic hydrocarbon group containing 6 to 10 carbon atoms and consisting of one or two rings which may be fused to each other or attached to each other via a single bond. Examples are phenyl, biphenyl, indenyl or naphthyl.

The term "heteroaryl", as used herein, means an aromatic or partially aromatic group consisting of one or two rings, which may be fused to each other or attached to each other via a single bond, and containing 5 to 10 ring atoms wherein up to four, preferably one, two or three ring atoms are heteroatom(s) and the remaining ring atoms are carbon. Examples of such heteroaryls include but are not limited to pyrrolyl, thiophenyl, furanyl, imidazolyl, pyrazolyl, triazolyl, oxazolyl, isoxazolyl, isothiazolyl, pyridinyl, pyrazinyl, triazinyl, tetrazinyl, quinolinyl, quinoxalinyl, chromanyl, benzoimidazolyl, indolyl, benzo[b]thiophenyl.

The term "halogen" means fluorine, chlorine, bromine or iodine.

The term "several times substituted" as used herein means up to 5 times substituted, preferably up to 4 times, most preferably 2 or 3 times substituted.

Compounds of the general formula I which contain one or several chiral centers can either be present in a racemic or in an optically active form. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457.

In one preferred embodiment according to the present invention, there are provided compounds of formula (I) as defined above, wherein $R^1$ is phenyl or pyridinyl, which may be both either unsubstituted or once or several times substituted by halogen; lower alkyl, which is unsubstituted or once or several times substituted by halogen; lower alkoxy; cycloalkyl; cyano; $NR^aR^b$; —$OCF_3$; or —$S(O)_2$-lower alkyl; and all remaining substituents have the significances given herein before.

In another preferred embodiment according to the present invention, there are provided compounds of formula (I) as defined herein before, wherein $R^1$ is phenyl, which is once or twice substituted by a substituent independently selected from the group consisting of: halogen; lower alkyl; —$CF_3$; cyclopropyl; cyano; —$OCF_3$; and —$S(O)_2$-lower alkyl;

$R^2$ and $R^3$, together with the carbon atoms to which they are attached, form a 4 to 6 membered cycloalkyl or a 4 to 6 membered heterocyclyl wherein one ring atom is a heteroatom which is oxygen; or $R^2$ is selected from the group consisting of: hydrogen; hydroxy; methoxy; piperidinyl; pyrrolidinyl; and —NRR' and $R^3$ is hydrogen; and $R^4$ is hydrogen; and all remaining substituents have the significances given herein before.

In still another preferred embodiment according to the present invention, there are provided compounds of formula (I) as defined above, wherein $R^1$ is cycloalkyl or heterocyclyl, and all remaining substituents have the significances given herein before.

In yet another preferred embodiment according to the present invention, there are provided compounds of formula (I) as defined above, wherein $R^1$ is selected from the group consisting of: cyclopentyl, cyclohexyl, piperidinyl, and tetrahydro-pyran;

$R^2$ is hydroxy; and $R^3$ and $R^4$ are hydrogen.

The following specific compounds are especially preferred according to the present invention:

(E)-N-(2-Amino-phenyl)-3-{4-[(4-cyclopropyl-phenylcarbamoyl)-((S)-3-hydroxy-pyrrolidin-1-yl)-methyl]-phenyl}-acrylamide;

(E)-N-(2-Amino-phenyl)-3-{4-[(4-chloro-phenylcarbamoyl)-(3-diethylamino-pyrrolidin-1-yl)-methyl]-phenyl}-acrylamide;

(E)-N-(2-Amino-phenyl)-3-{4-[(4-bromo-phenylcarbamoyl)-((S)-3-hydroxy-pyrrolidin-1-yl)-methyl]-phenyl}-acrylamide;

(E)-N-(2-Amino-phenyl)-3-{4-[(4-bromo-phenylcarbamoyl)-((R)-3-hydroxy-pyrrolidin-1-yl)-methyl]-phenyl}-acrylamide;

(E)-N-(2-Amino-phenyl)-3-{4-[(1S,4S)-(4-bromo-phenylcarbamoyl)-2-oxa-5-aza-bicyclo[2.2.1]hept-5-yl-methyl]-phenyl}-acrylamide;

(E)-N-(2-Amino-phenyl)-3-{4-[((R)-3-dimethylamino-pyrrolidin-1-yl)-(4-trifluoromethyl-phenylcarbamoyl)-methyl]-phenyl}-acrylamide;

(E)-N-(2-Amino-phenyl)-3-{4-[(3-diethylamino-pyrrolidin-1-yl)-(4-trifluoromethyl-phenylcarbamoyl)-methyl]-phenyl}-acrylamide;

(E)-N-(2-Amino-phenyl)-3-{4-[((S)-3-hydroxy-pyrrolidin-1-yl)-(4-trifluoromethyl-phenylcarbamoyl)-methyl]-phenyl}-acrylamide;

(E)-N-(2-Amino-phenyl)-3-{4-[((S)-3-hydroxy-pyrrolidin-1-yl)-(4-isopropyl-phenylcarbamoyl)-methyl]-phenyl}-acrylamide;

(E)-N-(2-Amino-phenyl)-3-{4-[(4-chloro-phenylcarbamoyl)-((S)-3-hydroxy-pyrrolidin-1-yl)-methyl]-phenyl}-acrylamide;

(E)-N-(2-Amino-phenyl)-3-{4-[(4-cyano-phenylcarbamoyl)-((S)-3-hydroxy-pyrrolidin-1-yl)-methyl]-phenyl}-acrylamide;
(E)-N-(2-Amino-phenyl)-3-{4-[(4-fluoro-phenylcarbamoyl)-((S)-3-hydroxy-pyrrolidin-1-yl)-methyl]-phenyl}-acrylamide;
(E)-N-(2-Amino-phenyl)-3-{4-[(3-diethylamino-pyrrolidin-1-yl)-(4-isopropyl-phenylcarbamoyl)-methyl]-phenyl}-acrylamide;
(E)-N-(2-Amino-phenyl)-3-{4-[(4-cyclopropyl-phenylcarbamoyl)-(3-diethylamino-pyrrolidin-1-yl)-methyl]-phenyl}-acrylamide;
(E)-N-(2-Amino-phenyl)-3-{4-[(4-cyano-phenylcarbamoyl)-(3-diethylamino-pyrrolidin-1-yl)-methyl]-phenyl}-acrylamide;
(E)-N-(2-Amino-phenyl)-3-{4-[(3-diethylamino-pyrrolidin-1-yl)-(4-fluoro-phenylcarbamoyl)-methyl]-phenyl}-acrylamide;
(E)-N-(2-Amino-phenyl)-3-{4-[(4-bromo-phenylcarbamoyl)-(3-diethylamino-pyrrolidin-1-yl)-methyl]-phenyl}-acrylamide;
(E)-N-(2-Amino-phenyl)-3-{4-[(2-fluoro-4-trifluoromethyl-phenylcarbamoyl)-((S)-3-hydroxy-pyrrolidin-1-yl)-methyl]-phenyl}-acrylamide;
(E)-N-(2-Amino-phenyl)-3-{4-[((S)-3-hydroxy-pyrrolidin-1-yl)-(6-trifluoromethyl-pyridin-3-ylcarbamoyl)-methyl]-phenyl}-acrylamide;
(E)-N-(2-Amino-phenyl)-3-{4-[((S)-3-hydroxy-pyrrolidin-1-yl)-(4-trifluoromethoxy-phenylcarbamoyl)-methyl]-phenyl}-acrylamide;
(E)-3-{4-[[3-(Acetyl-methyl-amino)-pyrrolidin-1-yl]-(4-trifluoromethyl-phenylcarbamoyl)-methyl]-phenyl}-N-(2-amino-phenyl)-acrylamide;
(E)-N-(2-Amino-phenyl)-3-(4-{(4-bromo-phenylcarbamoyl)-[3-(1-hydroxy-1-methyl-ethyl)-pyrrolidin-1-yl]-methyl}-phenyl)-acrylamide;
(E)-N-(2-Amino-phenyl)-3-[4-((4-bromo-phenylcarbamoyl)-{3-[ethyl-(2-hydroxy-ethyl)-amino]-pyrrolidin-1-yl}-methyl)-phenyl]-acrylamide;
(E)-N-(2-Amino-phenyl)-3-{4-[(4-bromo-phenylcarbamoyl)-(3-piperidin-1-yl-pyrrolidin-1-yl)-methyl]-phenyl}-acrylamide; and
(E)-N-(2-Amino-phenyl)-3-{4-[(3-diethylamino-pyrrolidin-1-yl)-(4-methanesulfonyl-phenylcarbamoyl)-methyl]-phenyl}-acrylamide.

The compounds according to the present invention show valuable pharmaceutical properties, in particular as anti-proliferative or anti-cancer agents, more specifically as agents for the treatment of solid tumors and hematological tumors.

Therefore, in another embodiment according to the present invention, there is provided a pharmaceutical composition comprising a compound as defined above and a pharmaceutically acceptable adjuvant.

In another embodiment according to the present invention, there is provided a compound as defined above for use as a medicament.

In still another embodiment according to the present invention, there is provided a compound as defined above for use in the treatment of cancer, in particular solid tumors and hematological tumors, more particularly leukemia, lymphoma, colon, liver, or gastric cancer.

In yet another embodiment according to the present invention, there is provided the use of at least one compound as defined above for the manufacture of medicaments for the treatment of cancer, in particular solid tumors and hematological tumors. Said medicaments, e.g. in the form of pharmaceutical preparations, can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

In another preferred embodiment according to the present invention, there is provided a method of treating cancer in a patient comprising administering to said patient at least one compound according to the present invention.

The compounds of the present invention as well as their starting materials can be synthesized according to the following general reaction schemes 1 to 4, respectively. In said reaction schemes 1 to 4 all substituents, in particular $R^1$ to $R^4$, have the meanings given herein before unless explicitly otherwise stated. Furthermore, and unless explicitly otherwise stated, all reactions, reaction conditions, abbreviations and symbols have the meanings well known to a person of ordinary skill in organic chemistry.

Therefore, in still another preferred embodiment according to the present invention, there is provided a process for the manufacture of the compounds of formula (I) according to the present invention, wherein the reaction partners and -conditions are as described in the following reaction scheme 1.

A. General Synthetic Route for Synthesis of Pyrrolidine-cinnamides (Scheme 1)

scheme 1

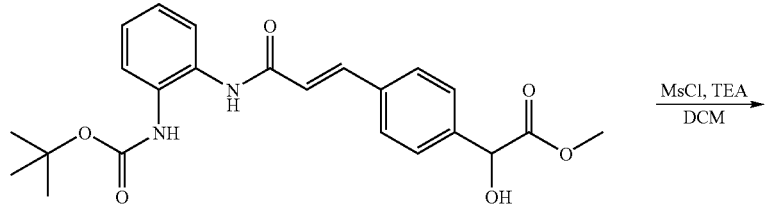

-continued
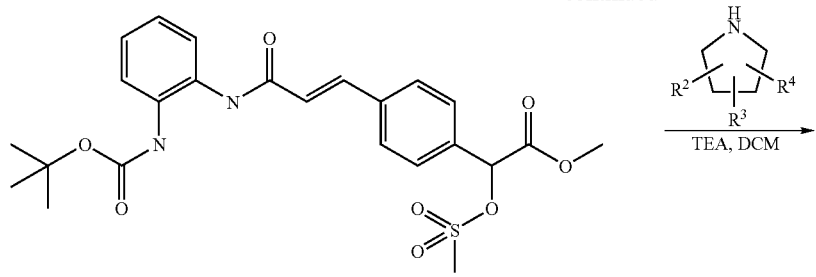
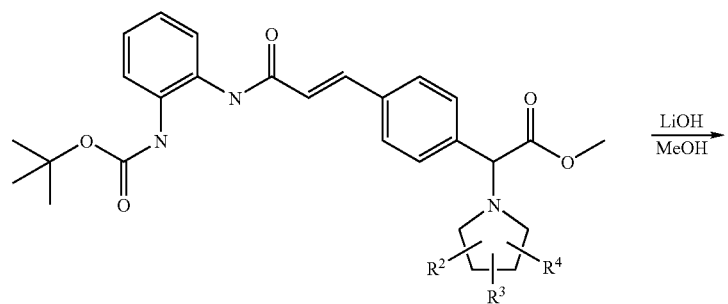
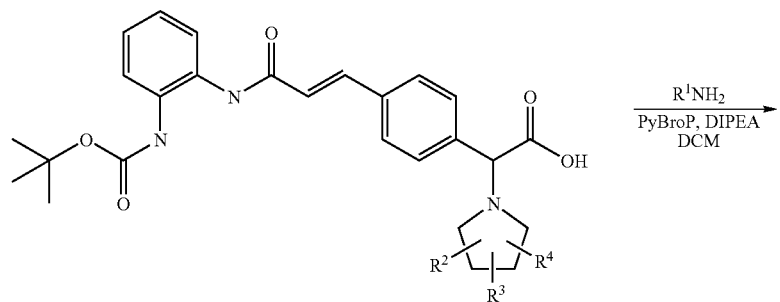
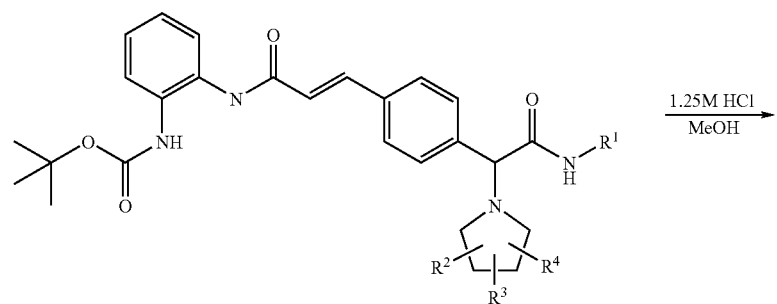
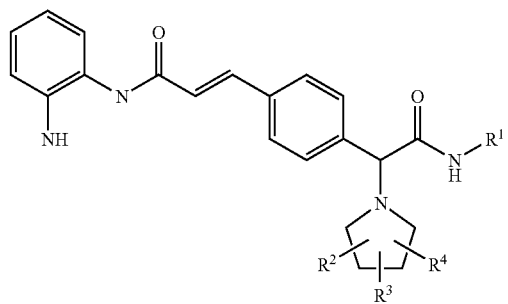

B. Synthetic Routes for Key Building Blocks

Synthesis of (2-acryloylamino-phenyl)-carbamic acid tert-butyl ester (scheme 2)

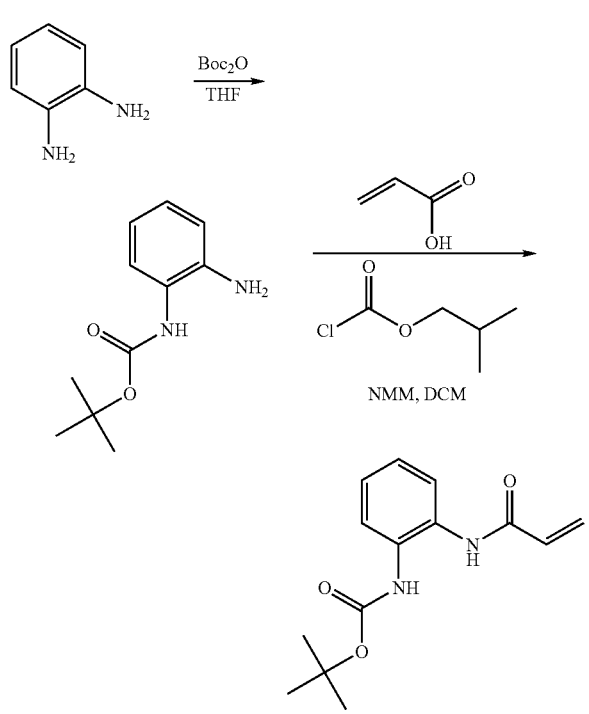

Synthesis of (E)-{2-[3-(4-Formyl-phenyl)-acryloylamino]-phenyl}-carbamic acid tert-butyl ester (scheme 3)

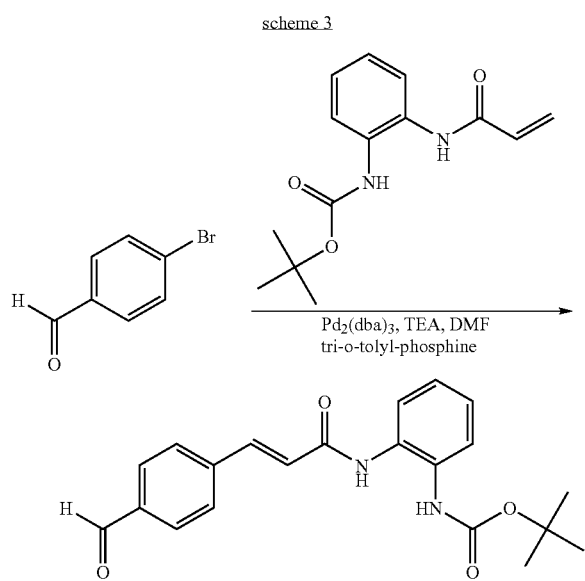

Synthesis of (E)-{4-[2-(2-tert-Butoxycarbonylamino-phenylcarbamoyl)-vinyl]-phenyl}-hydroxy-acetic acid methyl ester (scheme 4)

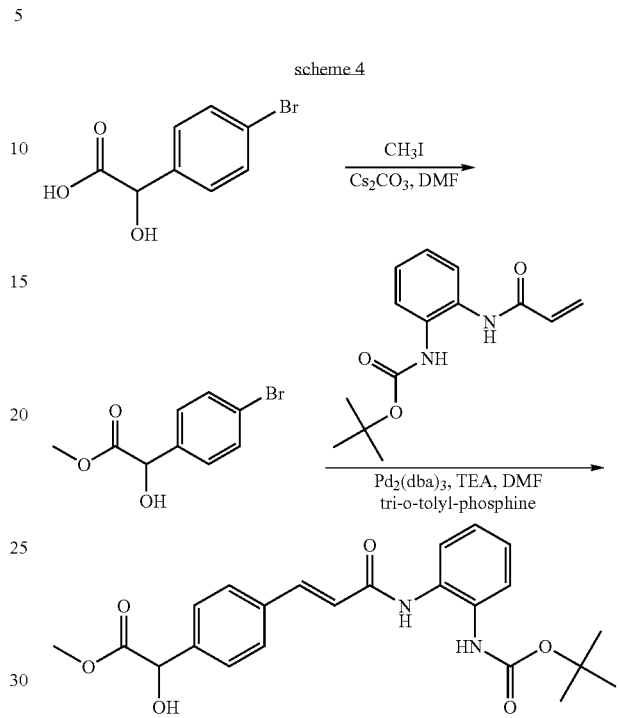

The following examples were prepared by the general methods outlined in the schemes above. They are intended to illustrate the meaning of the present invention but should by no means represent a limitation within the meaning of the present invention:

EXAMPLES

Example 1

(E)-{4-[2-(2-tert-Butoxycarbonylamino-phenylcarbamoyl)-vinyl]-phenyl}-methanesulfonyloxy-acetic acid methyl ester To a solution of {4-[2-(2-tert-butoxycarbonylamino-phenylcarbamoyl)-vinyl]-phenyl}-hydroxy-acetic acid methyl ester (9.00 g, 21.1 mmol) and triethylamine (3.20 g, 31.6 mmol) in $CH_2Cl_2$ (135 mL) cooled to −5 degrees Celsius was added dropwise methanesulfonyl chloride (3.14 g, 27.4 mmol) under $N_2$ atmosphere. The reaction was stirred at 0 degrees Celsius until the starting material had been consumed according to TLC (about 1 hour). The mixture was washed with water (90 mL) and brine (90 mL), dried with MgSO$_4$, filtered, and evaporated in vacuo to obtain 11.2 g (quantitative yield) of light yellow crystal which was used without further purification. MS: calc'd 505 (MH+), exp 505 (MH+).

Example 2

(E)-{4-[2-(2-tert-Butoxycarbonylamino-phenylcarbamoyl)-vinyl]-phenyl}-((S)-3-hydroxy-pyrrolidin-1-yl)-acetic acid methyl ester

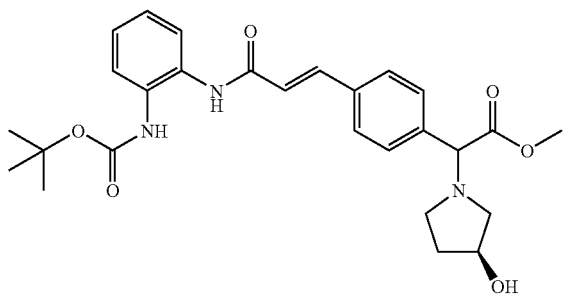

To a solution of {4-[2-(2-tert-butoxycarbonylamino-phenylcarbamoyl)-vinyl]-phenyl}-methanesulfonyloxy-acetic acid methyl ester (1.26 g, 2.5 mmol) and Et$_3$N (0.76 g, 7.5 mmol) in CH$_2$Cl$_2$ (15mL) was added (S)-3-hydroxypyrrolidine (0.27 g, 3 mmol). This mixture was stirred overnight at room temperature, then diluted with CH$_2$Cl$_2$ (50 mL), washed with saturated aqueous NaHCO$_3$ solution, water and brine, dried with Na$_2$SO$_4$, filtered, and evaporated to obtain a yellow solid which was directly used in the next reaction without further purification. MS: calc'd 496 (MH+), exp 496 (MH+).

Example 3

(E)-{4-[2-(2-tert-Butoxycarbonylamino-phenylcarbamoyl)-vinyl]-phenyl}-((S)-3-hydroxy-pyrrolidin-1-yl)-acetic acid

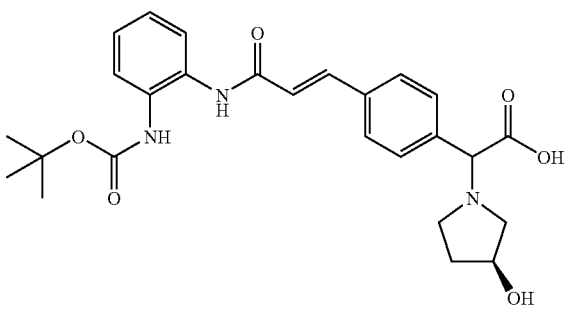

To a solution of {4-[2-(2-tert-butoxycarbonylamino-phenylcarbamoyl)-vinyl]-phenyl}-(3-hydroxy-pyrrolidin-1-yl)-acetic acid methyl ester (1.23 g, 2.5 mmol) in MeOH (30 mL) was added aqueous LiOH (1 N, 10 mL), This mixture was stirred for about 5 h at room temperature, and then evaporated to remove most of the MeOH. The aqueous layer was acidified with concentrated HCl to pH 5-6. The acidified aqueous layer was extracted with ethyl acetate (3×30 mL). The combined organic layer was washed with brine, dried with Na$_2$SO$_4$, filtered, and evaporated to obtain 0.85 g (81%) of a yellow solid product. MS: calc'd 482 (MH+), exp 482 (MH+).

Example 4

(E)-N-(2-Amino-phenyl)-3-{4-[(4-cyclopropyl-phenylcarbamoyl)-((S)-3-hydroxy-pyrrolidin-1-yl)-methyl]-phenyl}-acrylamide

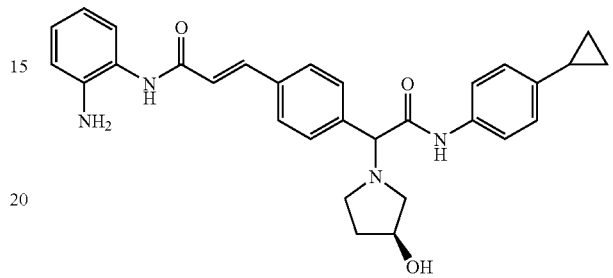

To a solution of {4-[2-(2-tert-butoxycarbonylamino-phenylcarbamoyl)-vinyl]-phenyl}-(3-hydroxy-pyrrolidin-1-yl)-acetic acid (200 mg, 0.42 mmol), PyBroP (290 mg, 0.62 mmol) and DIPEA (162 mg, 1.26 mol) in CH$_2$Cl$_2$ (10 mL) was added 4-cyclopropyl-phenylamine (100 mg, 0.75 mmol). This mixture was stirred overnight at room temperature and then diluted with CH$_2$Cl$_2$ (20 mL), washed with saturated aqueous NaHCO$_3$ solution, water and brine, dried with Na$_2$SO$_4$, and evaporated to obtain a yellow residue. Hydrochloric acid in methanol (1.25 M, 5 mL) was added to the residue, the mixture was stirred for about 3 h, and then NaHCO$_3$ was added to the reaction system. After filtration of solids, the crude mixture was purified by preparative HPLC to obtain 42.3 mg pale-yellow solid. MS: calc'd 497 (MH+), exp 497 (MH+). $^1$H NMR (d$_4$-MeOD, 400 MHz) 7.70 (m, 5H), 7.45 (m, 2H), 7.21 (m, 1H), 7.04 (m, 3H), 6.88 (m, 2H), 6.76 (m, 1H), 4.35 (m, 1H), 3.98(s, 1H, epimer A), 3.97 (s, 1H, epimer B), 3.00 (m, 1H), 2.56-1.85(m, 6H), 0.94(m, 2H), 0.64 (m, 2H).

Example 5

(E)-{4-[2-(2-tert-Butoxycarbonylamino-phenylcarbamoyl)-vinyl]-phenyl}-(3-diethylamino-pyrrolidin-1-yl)-acetic acid methyl ester

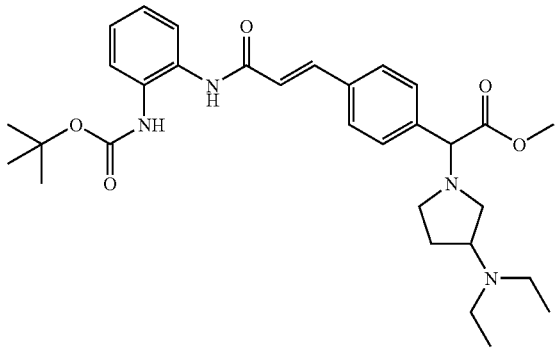

To a solution of {4-[2-(2-tert-butoxycarbonylamino-phenylcarbamoyl)-vinyl]-phenyl}-methanesulfonyloxy-acetic acid methyl ester (1.89 g, 3.75 mmol) and Et₃N (1.46 g, 14.4 mmol) in CH₂Cl₂ (30 mL) was added (S)-3-hydroxypyrrolidine (0.67 g, 4.5 mmol). This mixture was stirred overnight at room temperature, then diluted with CH₂Cl₂ (50 mL), washed with saturated aqueous NaHCO₃ solution, water and brine, dried with Na₂SO₄, filtered, and evaporated to obtain a yellow solid which was directly used in the next reaction without further purification. MS: calc'd 551 (MH+), exp 551 (MH+).

Example 6

(E)-{4-[2-(2-tert-Butoxycarbonylamino-phenylcarbamoyl)-vinyl]-phenyl}-(3-diethylamino-pyrrolidin-1-yl)-acetic acid

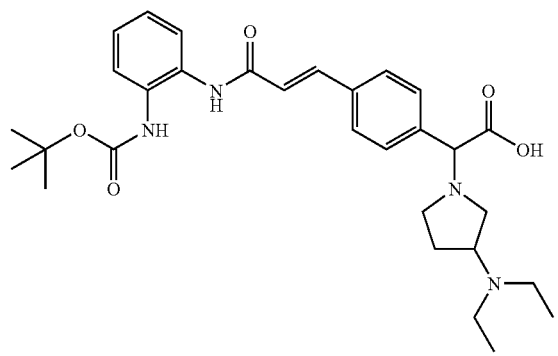

To a solution of {4-[2-(2-tert-butoxycarbonylamino-phenylcarbamoyl)-vinyl]-phenyl}-(3-diethylamino-pyrrolidin-1-yl)-acetic acid methyl ester (2.06 g, 3.75 mmol) in MeOH (30 mL) was added aqueous LiOH (1 N, 15 mL), This mixture was stirred for about 5 h at room temperature, and then evaporated to remove most of the MeOH. The aqueous layer was acidified with concentrated HCl to pH 5-6. The acidified aqueous layer was extracted with ethyl acetate (3×30 mL). The combined organic layer was washed with brine, dried with Na₂SO₄, filtered, and evaporated to obtain 1.40 g (70%) of yellow solid product. MS: calc'd 537 (MH+), exp 537 (MH+).

Example 7

(E)-N-(2-Amino-phenyl)-3-(4-{(4-chloro-phenylcarbamoyl)-[3-(1-ethyl-propyl)-pyrrolidin-1-yl]-methyl}-phenyl)-acrylamide

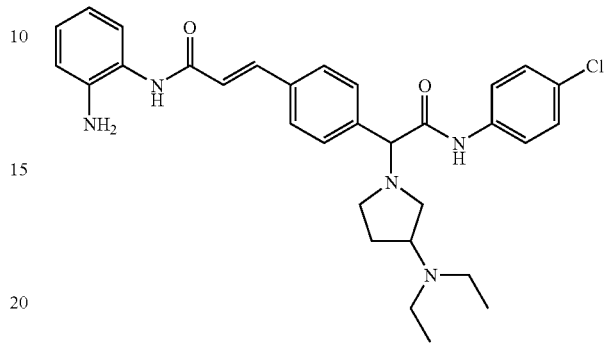

To a solution of {4-[2-(2-tert-butoxycarbonylamino-phenylcarbamoyl)-vinyl]-phenyl}-(3-diethylamino-pyrrolidin-1-yl)-acetic acid (200 mg, 0.37 mmol), PyBroP (300 mg, 0.64 mmol) and DIPEA (162 mg, 1.26 mol) in CH₂Cl₂ (10 mL) was added 4-chloro-phenylamine (100 mg, 0.78 mmol). This mixture was stirred overnight, and then diluted with CH₂Cl₂ (20 mL), washed with saturated aqueous NaHCO₃ solution, water and brine, dried with Na₂SO₄, and evaporated to obtain a yellow residue. A solution of hydrochloric acid in methanol (1.25 N, 5 mL) was added to the residue, the mixture was stirred for about 3 h, and then NaHCO₃ was added to the reaction system. After filtering to remove solids, the crude mixture was purified by preparative HPLC to obtain 25.5 mg pale-yellow solid. MS: calc'd 546 (MH+), exp 546 (MH+). ¹H NMR (d₄-MeOD, 400 MHz) 7.61 (m, 7H), 7.32 (m, 2H), 7.22 (m, 1H), 7.06 (m, 1H), 6.88 (m, 2H), 6.76 (m, 1H), 3.99 (s, 1H), 3.45 (m, 1H), 2.68 (m, 6H), 2.50 (m, 2H), 2.09 (m, 1H), 1.85 (m, 1H), 1.06 (m, 6H).

The compounds shown in the following Table 1 were prepared by methods analogous to the synthetic methods described above, but using the appropriate starting materials. The subsequently shown Table 2 shows the NMR-data for the compounds of Table 1.

TABLE 1

| Example # | Structure | MW | MS (MH+) calc'd | MS (MH+) exp |
|---|---|---|---|---|
| 7-1 | 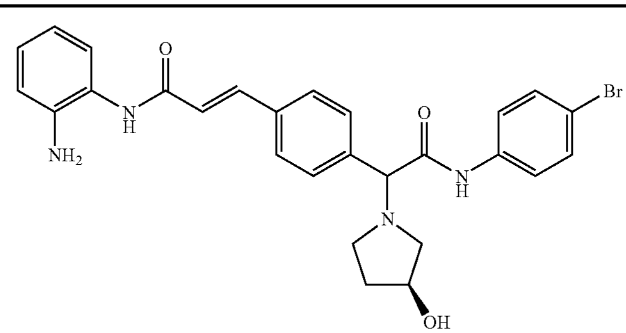 | 535.45 | 535 | 535 |

TABLE 1-continued

| Example # | Structure | MW | MS (MH+) calc'd | MS (MH+) exp |
|---|---|---|---|---|
| 7-2 | 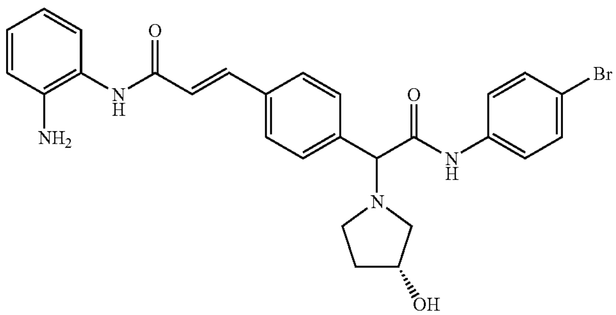 | 535.45 | 535 | 535 |
| 7-3 | 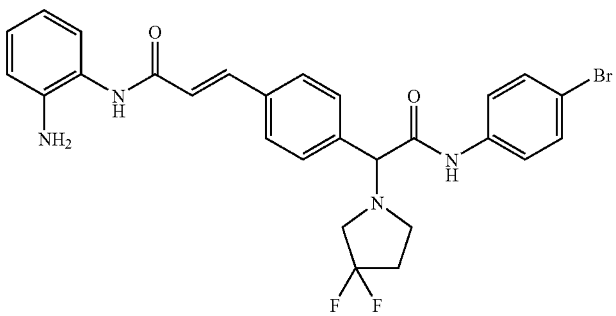 | 555.43 | 555 | 555 |
| 7-4 | 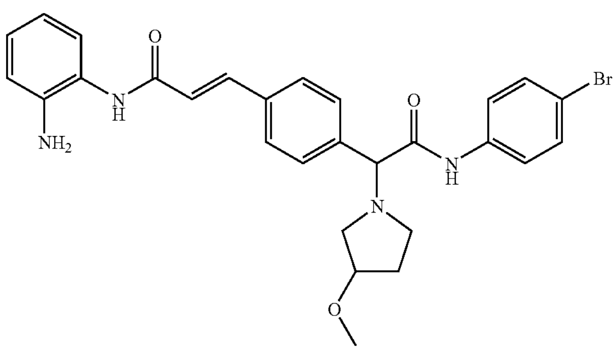 | 549.47 | 549 | 549 |
| 7-5 | 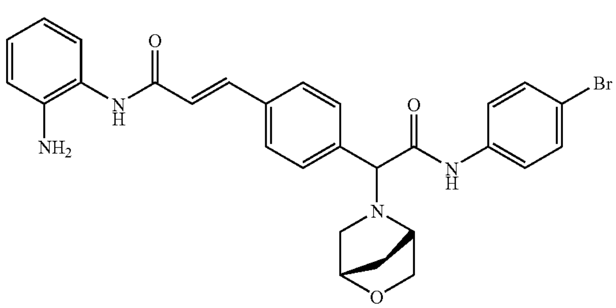 | 547.46 | 547 | 547 |

TABLE 1-continued

| Example # | Structure | MW | MS (MH+) calc'd | MS (MH+) exp |
|---|---|---|---|---|
| 7-6 | 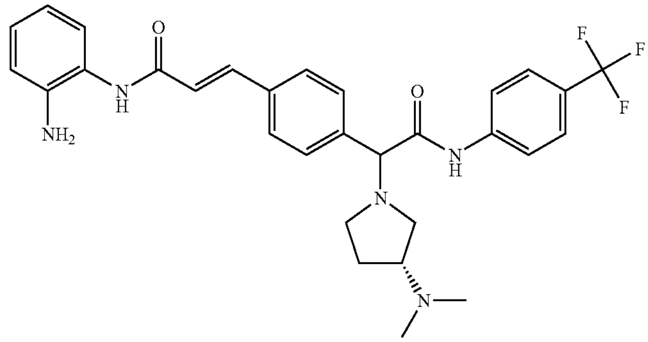 | 551.62 | 552 | 552 |
| 7-7 | 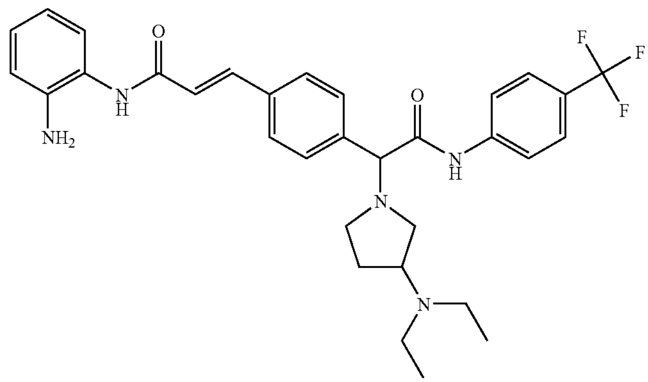 | 579.67 | 580 | 580 |
| 7-8 | 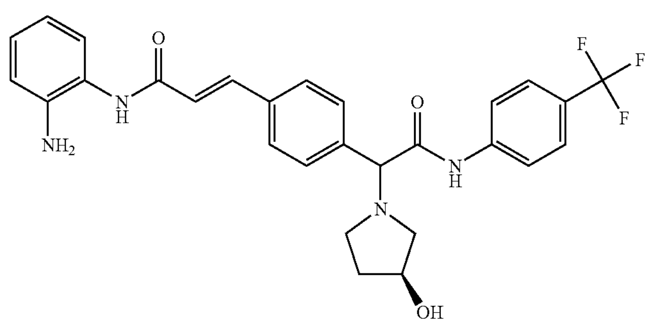 | 524.55 | 525 | 525 |
| 7-9 | 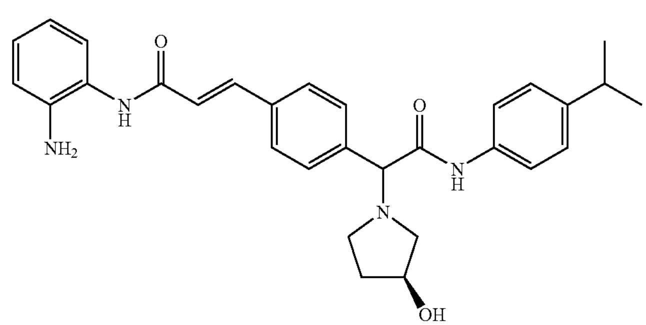 | 498.63 | 499 | 499 |

TABLE 1-continued

| Example # | Structure | MW | MS (MH+) calc'd | MS (MH+) exp |
|---|---|---|---|---|
| 7-10 | 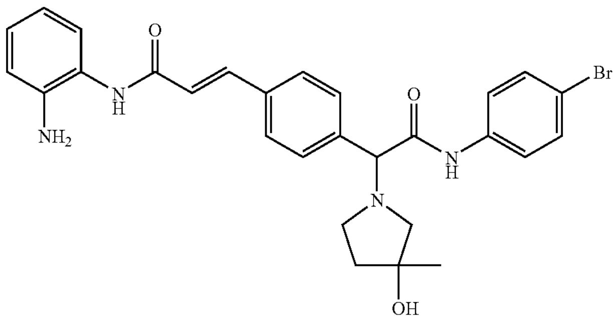 | 549.47 | 549 | 549 |
| 7-11 | 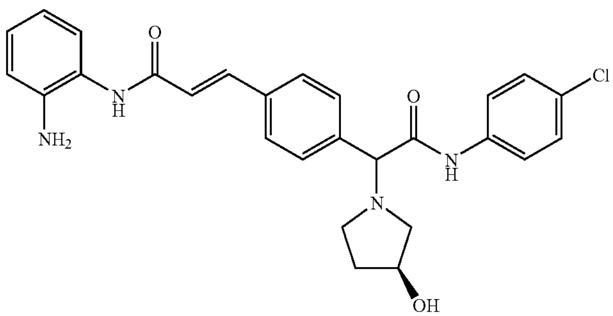 | 490.99 | 491 | 491 |
| 7-12 | 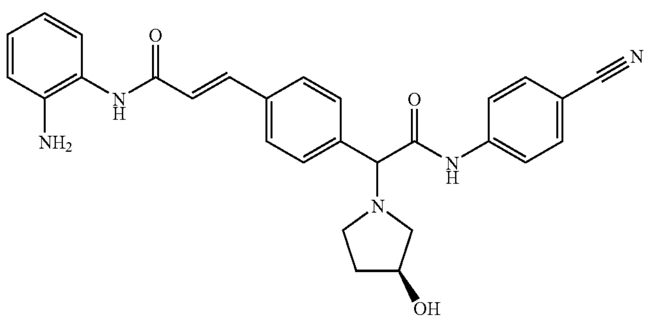 | 481.56 | 482 | 482 |
| 7-13 | 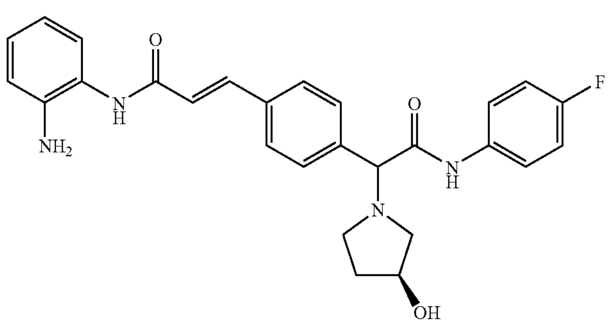 | 474.54 | 475 | 475 |

TABLE 1-continued

| Example # | Structure | MW | MS (MH+) calc'd | MS (MH+) exp |
|---|---|---|---|---|
| 7-14 | 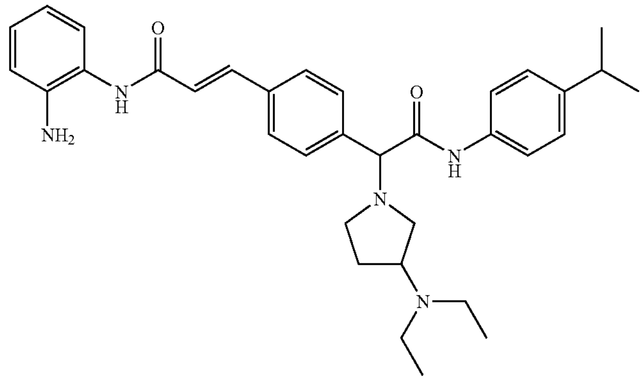 | 553.75 | 554 | 554 |
| 7-15 | 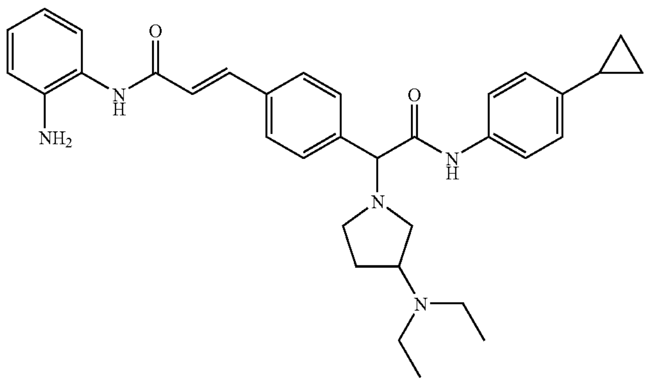 | 551.74 | 552 | 552 |
| 7-16 | 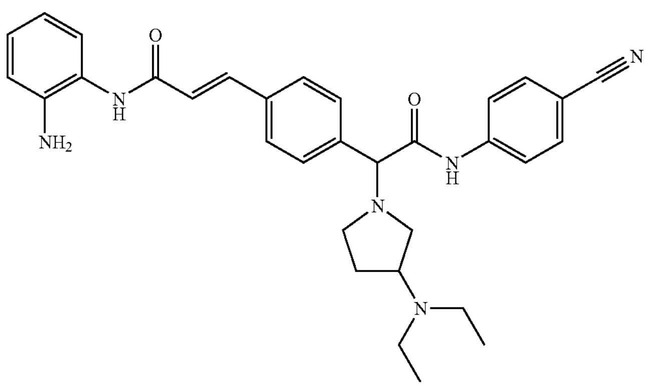 | 536.68 | 537 | 537 |
| 7-17 | 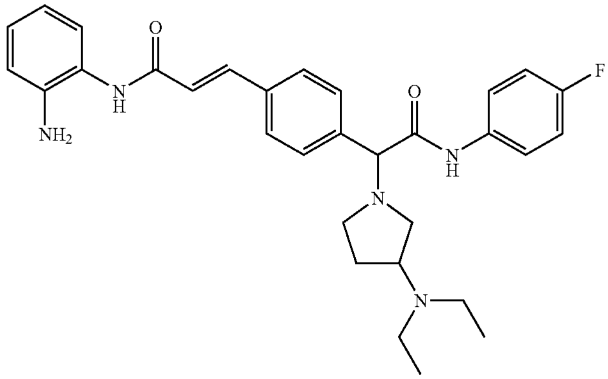 | 529.66 | 530 | 530 |

TABLE 1-continued

| Example # | Structure | MW | MS (MH+) calc'd | MS (MH+) exp |
|---|---|---|---|---|
| 7-18 | 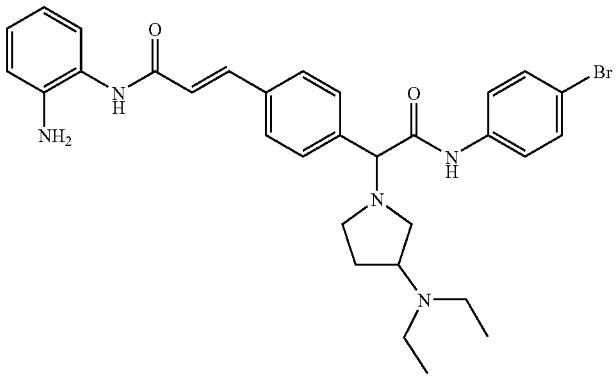 | 590.57 | 590 | 590 |
| 7-19 | 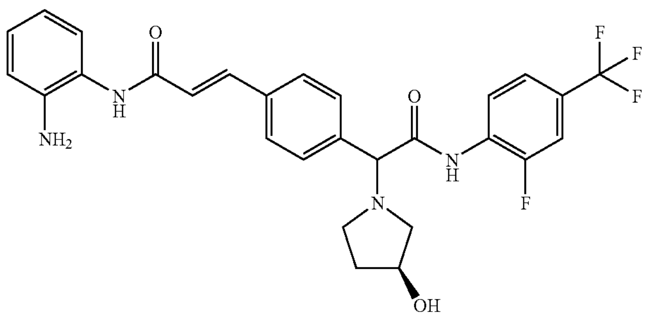 | 542.54 | 543 | 543 |
| 7-20 | 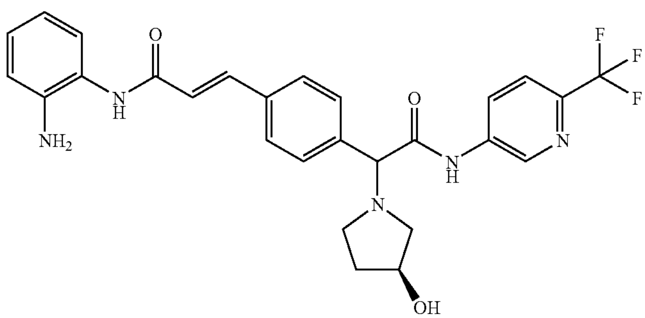 | 525.54 | 526 | 526 |
| 7-21 | 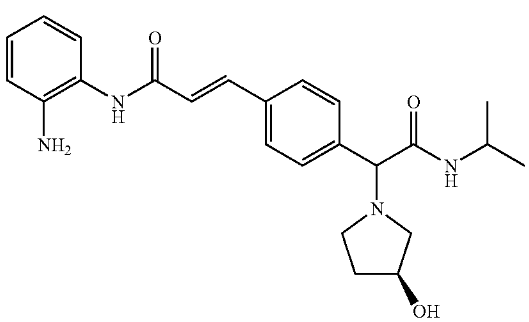 | 422.53 | 423 | 423 |

TABLE 1-continued
| Example # | Structure | MW | MS (MH+) calc'd | MS (MH+) exp |
|---|---|---|---|---|
| 7-22 | 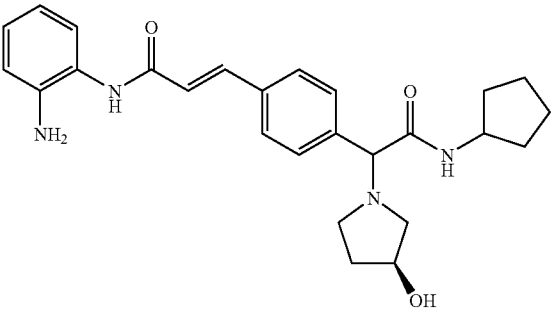 | 448.57 | 449 | 449 |
| 7-23 | 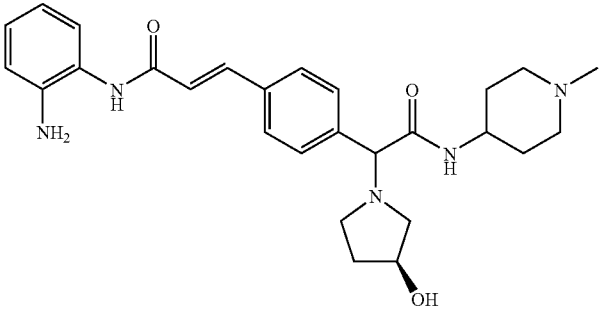 | 477.61 | 478 | 478 |
| 7-24 | 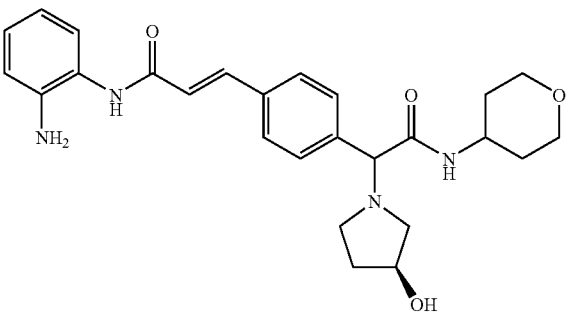 | 464.57 | 465 | 465 |
| 7-25 | 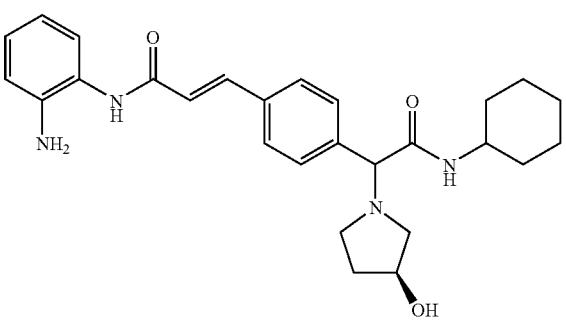 | 462.60 | 463 | 463 |
| 7-26 | 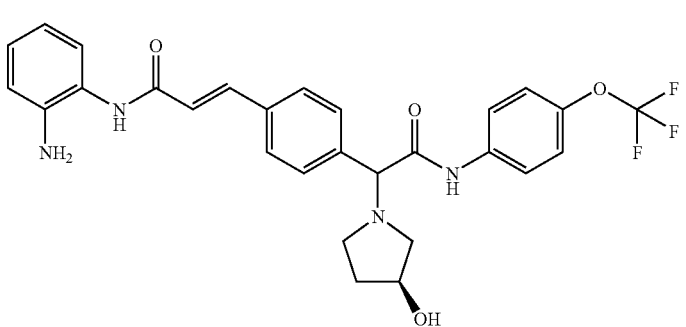 | 540.55 | 541 | 541 |

TABLE 1-continued

| Example # | Structure | MW | MS (MH+) calc'd | MS (MH+) exp |
|---|---|---|---|---|
| 7-27 | 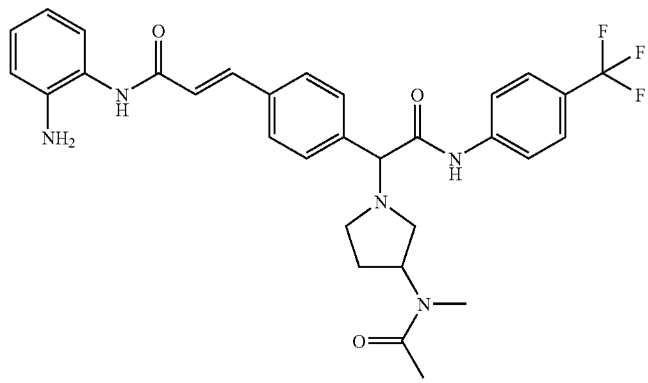 | 579.63 | 580 | 580 |
| 7-28 | 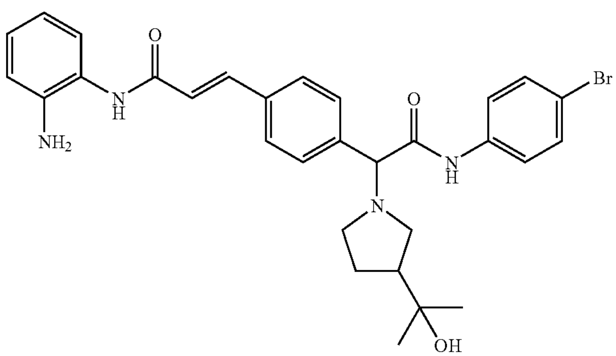 | 577.53 | 577 | 577 |
| 7-29 | 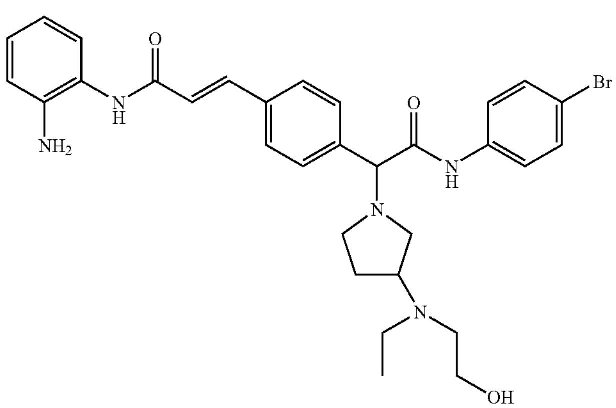 | 606.57 | 606 | 606 |
| 7-30 | 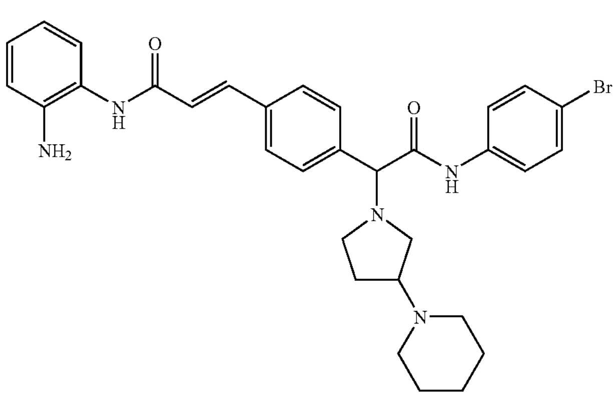 | 602.58 | 602 | 602 |

TABLE 1-continued

| Example # | Structure | MW | MS (MH+) calc'd | MS (MH+) exp |
| --- | --- | --- | --- | --- |
| 7-31 | 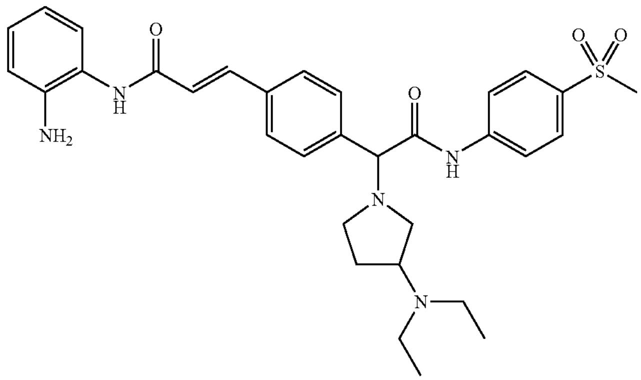 | 589.76 | 590 | 590 |

TABLE 2

| Example # | NMR data |
| --- | --- |
| 7-1 | $^1$H NMR (d$_4$-MeOD, 400 MHz) 7.83 (d, 2H, J = 8.0 Hz), 7.81 (d, 1H, J = 15.6 Hz), 7.75 (d, 2H, J = 8.0 Hz), 7.55 (d, 2H, J = 8.8 Hz), 7.49 (d, 2H, J = 8.8 Hz), 7.40-7.30 (m, 4H), 6.98 (d, 1H, J = 15.6 Hz), 5.24 (m, 1H), 4.60 (broad s, 1H), 4.00-3.80 (broad m, 2H), 3.60-3.20 (broad m, 2H), 2.35-2.15 (broad m, 2H). |
| 7-2 | $^1$H NMR (d$_4$-MeOD, 400 MHz) 7.83 (d, 2H, J = 8.0 Hz), 7.81 (d, 1H, J = 15.6 Hz), 7.75 (d, 2H, J = 8.0 Hz), 7.55 (d, 2H, J = 8.8 Hz), 7.49 (d, 2H, J = 8.8 Hz), 7.40-7.30 (m, 4H), 6.98 (d, 1H, J = 15.6 Hz), 5.24 (m, 1H), 4.60 (broad s, 1H), 4.00-3.80 (broad m, 2H), 3.60-3.20 (broad m, 2H), 2.35-2.15 (broad m, 2H). |
| 7-3 | $^1$H NMR (d$_4$-MeOD, 400 MHz) 7.83 (d, 1H, J = 15.6 Hz), 7.75 (d, 2H, J = 8.4 Hz), 7.71 (d, 2H, J = 8.4 Hz), 7.57 (d, 2H, J = 8.8 Hz), 7.50 (d, 2H, J = 8.8 Hz), 7.42-7.31 (m, 4H), 6.95 (d, 1H, J = 15.6 Hz), 4.33 (s, 1H), 3.22-2.81 (m, 4H), 2.45 (m, 2H). |
| 7-4 | $^1$H NMR (d$_4$-MeOD, 400 MHz) 7.85 (d, 2H, J = 8.4 Hz), 7.81 (d, 1H, J = 15.6 Hz), 7.77 (d, 2H, J = 8.4 Hz), 7.57 (d, 2H, J = 8.8 Hz), 7.52 (d, 2H, J = 8.8 Hz), 7.36-7.18 (m, 4H), 7.00 (d, 1H, J = 15.6 Hz), 5.17 (m, 1H), 4.25 (broad s, 1H), 3.80-3.50 (broad m, 2H), 3.42 (m, 4H), 3.30 (m, 1H), 2.40-2.20 (m, 2H). |
| 7-5 | $^1$H NMR (d$_4$-MeOD, 400 MHz) 7.85 (m, 5H), 7.55 (m, 4H), 7.35-7.10 (m, 4H), 7.02 (m, 1H), 5.25 (s, 1H), 4.76 (m, 1H), 4.50-4.30 (m, 2H), 3.90 (m, 1H), 3.29 (m, 2H), 2.45 (d, 1H, J = 11 Hz), 2.29 (d, 1H, J = 11 Hz). |
| 7-6 | $^1$H NMR (d$_4$-MeOD, 400 MHz) 7.81 (d, 2H, J = 8.4 Hz), 7.68 (d, 1H, J = 15.6 Hz), 7.65 (m, 4H), 7.62 (d, 2H, J = 8.4 Hz), 7.21 (dd, 1H, J = 8.0 Hz, 1.2 Hz), 7.06 (dt, 1H, J = 1.2 Hz, 8.4 Hz), 6.88 (d, 1H, J = 15.6 Hz), 6.87 (dd, 1H, J = 7.2 Hz, 1.2 Hz), 6.76 (dt, 1H, J = 1.2 Hz, 8.0 Hz), 4.03 (s, 1H), 2.90 (m, 1H), 2.82 (m, 1H), 2.75 (m, 1H), 2.55 (m, 2H), 2.29 (s, 6H), 2.10 (m, 1H), 1.83 (m, 1H). |
| 7-7 | $^1$H NMR (d$_4$-MeOD, 400 MHz) 7.79 (d, 2H, J = 8.4 Hz), 7.78 (d, 1H, J = 15.6 Hz), 7.70 (m, 4H), 7.62 (d, 2H, J = 8.4 Hz), 7.35-7.25 (m, 4H), 6.91 (d, 1H, J = 15.6 Hz), 4.34 (s, 1H), 4.12 (m, 1H), 3.45 (m, 2H), 3.30 (m, 3H), 2.90 (m, 2H), 2.55 (m, 1H), 2.35 (m, 1H), 2.10 (m, 1H), 1.38 (t, 6H, J = 7.2 Hz). |
| 7-8 | $^1$H NMR (d$_4$-MeOD, 400 MHz) 7.80 (m, 5H), 7.75 (d, 2H, J = 8.0 Hz), 7.65 (d, 2H, J = 8.0 Hz), 7.29 (d, 1H, J = 7.6 Hz), 7.22 (t, 1H, J = 7.6 Hz), 7.13 (d, 1H, J = 8.0 Hz), 7.06 (t, 1H, J = 7.2 Hz), 6.97 (d, 1H, J = 15.6 Hz), 5.27 (s, 1H, epimer A), 5.23 (s, 1H, epimer B), 4.62 (broad s, 1H), 3.90-3.60 (broad m, 2H), 3.50 (broad m, 1H), 3.25 (broad m, 1H), 2.35-2.10 (m, 2H). |
| 7-9 | $^1$H NMR (d$_4$-MeOD, 400 MHz) 7.82 (d, 2H, J = 8.4 Hz), 7.76 (d, 1H, J = 15.6 Hz), 7.75 (d, 2H, J = 8.4 Hz), 7.48 (d, 2H, J = 8.4 Hz), 7.25 (dd, 1H, J = 8.0 Hz, 1.2 Hz), 7.21 (d, 2H, J = 8.4 Hz), 7.16 (dt, 1H, J = 1.2 Hz, 8.0 Hz), 7.03 (d, 1H, J = 7.2 Hz), 6.96 (d, 1H, J = 15.6 Hz), 6.94 (t, 1H, J = 8.0 Hz), 5.10 (m, 1H), 4.61 (broad s, 1H), 3.70-3.10 (broad m, 4H), 2.90 (m, 1H), 2.20-2.00 (m, 2H), 1.25 (d, 6H, J = 6.8 Hz). |
| 7-10 | $^1$H NMR (d$_4$-MeOD, 400 MHz) 7.82 (d, 2H, J = 8.0 Hz), 7.76 (d, 1H, J = 15.6 Hz), 7.74 (d, 2H, J = 8.0 Hz), 7.54 (d, 2H, J = 8.8 Hz), 7.49 (d, 2H, J = 8.8 Hz), 7.29 (d, 1H, J = 8.0 Hz), 7.24 (t, 1H, J = 7.6 Hz), 7.15 (d, 1H, J = 7.6 Hz), 7.11 (t, 1H, J = 8.0 Hz), 6.96 (d, 1H, J = 15.6 Hz), 5.24 (s, 1H), 3.80-3.55 (broad m, 2H), 3.50 (m, 1H), 3.15 (m, 1H), 2.01 (m, 2H), 1.47 (s, 3H, racemic diastereomer A), 1.45 (s, 3H, racemic diastereomer B). |

TABLE 2-continued

| Example # | NMR data |
|---|---|
| 7-11 | $^1$H NMR (d$_4$-MeOD, 400 MHz) 7.68 (d, 1H, J = 15.6 Hz), 7.63 (m, 6H), 7.32 (dd, 2H, J = 9.2 Hz, 2.4 Hz), 7.22 (dd, 1H, J = 8.0 Hz, 1.2 Hz), 7.07 (dt, 1H, J = 1.2 Hz, 8.0 Hz), 6.88 (d, 1H, J = 15.6 Hz), 6.87 (dd, 1H, J = 8.0 Hz, 1.2 Hz), 6.77 (dt, 1H, J = 1.2 Hz, 8.0 Hz), 4.38 (m, 1H, epimer A), 4.35 (m, 1H, epimer B), 4.03 (s, 1H), 3.04-2.60 (m, 3H), 2.50 (m, 1H, epimer A), 2.45 (m, 1H, epimer B), 2.20 (m, 1H), 1.8 (m, 1H). |
| 7-12 | $^1$H NMR (d$_4$-MeOD, 400 MHz) 7.85 (m, 2H), 7.71-7.61 (m, 7H), 7.21 (dd, 2H, J = 7.6 Hz, 1.2 Hz), 7.07 (dt, 1H, J = 1.2 Hz, 8.0 Hz), 6.89 (d, 1H, J = 16 Hz), 6.87 (dd, 1H, J = 8.0 Hz, 1.2 Hz), 6.76 (dt, 1H, J = 1.2 Hz, 8.0 Hz), 4.36 (m, 1H, epimer A), 4.35 (m, 1H, epimer B), 4.09 (s, 1H), 3.15 (m, 1H, epimer A), 3.04 (m, 1H, epimer B), 2.80-2.45 (m, 3H), 2.20 (m, 1H), 1.8 (m, 1H). |
| 7-13 | $^1$H NMR (d$_4$-MeOD, 400 MHz) 7.68 (d, 1H, J = 16.0 Hz), 7.64-7.57 (m, 6H), 7.22 (dd, 1H, J = 8.0 Hz, 1.2 Hz), 7.09-7.05 (m, 3H), 6.89 (d, 1H, J = 16.0 Hz), 6.87 (d, 1H, J = 8.0 Hz), 6.78 (t, 1H, J = 7.2 Hz, 1.2 Hz), 4.40 (m, 1H, epimer A), 4.35 (m, 1H, epimer B), 4.00 (s, 1H), 3.05 (m, 1H, epimer A), 2.75 (m, 1H, epimer B), 2.70-2.55 (m, 2H), 2.45 (m, 1H, epimer A), 2.40 (m, 1H, epimer B), 2.00 (m, 1H), 1.80 (m, 1H). |
| 7-14 | $^1$H NMR (d$_4$-MeOD, 400 MHz) 7.68 (d, 1H, J = 15.6 Hz), 7.64 (m, 4H), 7.47 (d, 2H, J = 8.4 Hz, racemic diastereomer A), 7.46 (d, 2H, J = 8.4 Hz, racemic diastereomer B), 7.22 (dd, 1H, J = 8.0 Hz, 1.2 Hz, 7.19 (d, 2H, J = 8.4 Hz), 7.07 (dt, 1H, J = 1.2 Hz, 8.0 Hz), 6.88 (d, 1H, J = 15.6 Hz), 6.87 (dd, 1H, J = 8.4 Hz, 1.2 Hz), 6.76 (dt, 1H, J = 1.2 Hz, 8.4 Hz), 3.98 (s, 1H), 3.47 (m, 1H), 2.90-2.50 (m, 9H), 2.10 (m, 1H), 1.85 (m, 1H), 1.22 (d, 6H, J = 6.9 Hz), 1.08 (t, 6H, J = 7.2 Hz). |
| 7-15 | $^1$H NMR (d$_4$-MeOD, 400 MHz) 7.68 (d, 1H, J = 15.6 Hz), 7.64 (m, 4H), 7.44 (d, 2H, J = 8.4 Hz, racemic diastereomer A), 7.42 (d, 2H, J = 8.4 Hz, racemic diastereomer B), 7.22 (dd, 1H, J = 8.0 Hz, 1.2 Hz), 7.06 (dt, J = 1.2 Hz, 8.4 Hz), 7.03 (d, 2H, J = 8.4 Hz), 6.89 (dd, 1H, J = 8.0 Hz, 1.2 Hz), 6.88 (d, 1H, J = 15.6 Hz), 6.76 (dt, 1H, J = 1.2 Hz, 8.0 Hz), 3.97 (s, 1H), 3.44 (m, 1H), 2.80-2.50 (m, 8H), 2.08 (m, 1H), 1.85 (m, 1H), 1.05 (t, 6H, J = 7.2 Hz), 0.95 (m, 2H), 0.65 (m, 2H). |
| 7-16 | $^1$H NMR (d$_4$-MeOD, 400 MHz) 7.83 (m, 2H), 7.70-7.61 (m, 7H), 7.21 (dd, 1H, J = 8.0 Hz, 1.2 Hz), 7.07 (dt, 1H, J = 1.2 Hz, 8.0 Hz), 6.88 (d, 1H, J = 15.6 Hz), 6.87 (dd, 1H, J = 8.0 Hz, 1.2 Hz), 6.76 (dt, 1H, J = 1.2 Hz, 8.0 Hz), 4.04 (s, 1H), 3.45 (m, 1H), 2.85-2.50 (m, 8H), 2.08 (m, 1H), 1.85 (m, 1H), 1.05 (m, 6H). |
| 7-17 | $^1$H NMR (d$_4$-MeOD, 400 MHz) 7.68 (d, 1H, J = 15.6 Hz), 7.65-7.55 (m, 6H), 7.22 (dd, 1H, J = 8.0 Hz, 1.2 Hz), 7.10-7.03 (m, 3H), 6.88 (d, 1H, J = 15.6 Hz), 6.87 (dd, 1H, J = 8.0 Hz, 1.2 Hz), 6.76 (dt, 1H, J = 1.2 Hz, 8.0 Hz), 3.98 (s, 1H), 3.43 (m, 1H), 2.81-2.48 (m, 8H), 2.08 (m, 1H), 1.83 (m, 1H), 1.05 (m, 6H). |
| 7-18 | $^1$H NMR (d$_4$-MeOD, 400 MHz) 7.68 (d, 1H, J = 15.6 Hz), 7.63 (m, 4H), 7.57-7.51 (m, 2H), 7.45 (d, 2H, J = 9.2 Hz), 7.22 (d, 1H, J = 8.0 Hz), 7.06 (t, 1H, J = 8.0 Hz), 6.88 (d, 1H, J = 15.6 Hz), 6.87 (d, J = 8.0 Hz), 6.76 (t, 1H, J = 8.0 Hz), 3.99 (s, 1H), 3.38 (m, 2H), 2.80-2.50 (m, 7H), 2.05 (m, 1H), 1.80 (m, 1H), 1.05 (m, 6H). |
| 7-19 | $^1$H NMR (d$_4$-MeOD, 400 MHz) 8.13 (m, 1H), 7.72-7.61 (m, 5H), 7.53 (m, 2H), 7.22 (d, 1H, J = 8.0 Hz), 7.07 (t, 1H, J = 8.0 Hz), 6.92-6.88 (m, 2H), 6.77 (t, 1H, J = 8.0 Hz), 4.38 (m, 1H), 4.18 (m, 1H), 3.15 (m, 1H, epimer A), 3.04 (m, 1H, epimer B), 2.85-2.45 (m, 3H), 2.20 (m, 1H), 1.85 (m, 1H). |
| 7-20 | $^1$H NMR (d$_4$-MeOD, 400 MHz) 8.94 (s, 1H), 8.40 (d, 1H, J = 8.8 Hz), 7.80-7.50 (m, 6H), 7.22 (d, 1H, J = 8.0 Hz), 7.07 (t, 1H, J = 8.0 Hz), 6.89 (m, 2H), 6.76 (t, 1H, J = 8.0 Hz), 4.40 (m, 1H, epimer A), 4.36 (m, 1H, epimer B), 4.18 (s, 1H), 3.15 (m, 1H, epimer A), 3.04 (m, 1H, epimer B), 2.85-2.40 (m, 3H), 2.20 (m, 1H), 1.85 (m, 1H). |
| 7-21 | $^1$H NMR (d$_4$-MeOD, 400 MHz) 7.68 (d, 1H, J = 15.6 Hz), 7.65 (d, 2H, J = 8.8 Hz), 7.55 (d, 2H, J = 6.8 Hz), 7.22 (d, 1H, J = 8.0 Hz), 7.07 (t, 1H, J = 8.0 Hz), 6.89 (m, 2H), 6.76 (t, 1H, J = 8.0 Hz), 4.38 (m, 1H, epimer A), 4.36 (m, 1H, epimer B), 4.00 (m, 1H), 3.95 (m, 1H), 3.20 (m, 1H, epimer A), 3.00 (m, 1H, epimer B), 2.80-2.35 (m, 3H), 2.20 (m, 1H), 1.80 (m, 1H), 1.17 (m, 6H). |
| 7-22 | $^1$H NMR (d$_4$-MeOD, 400 MHz) 7.68 (d, 1H, J = 15.6 Hz), 7.62 (d, 2H, J = 8.0 Hz), 7.55 (d, 2H, J = 7.2 Hz), 7.22 (d, 1H, J = 8.0 Hz), 7.07 (t, 1H, J = 8.0 Hz), 6.89 (m, 2H), 6.76 (t, 1H, J = 8.0 Hz), 4.35 (m, 1H, epimer A), 4.33 (m, 1H, epimer B), 4.10 (m, 1H), 3.88 (m, 1H), 3.18 (m, 1H, epimer A), 2.95 (m, 1H, epimer B), 2.80-2.10 (m, 4H), 2.00-1.40 (m, 9H). |
| 7-23 | $^1$H NMR (d$_4$-MeOD, 400 MHz) 7.68 (d, 1H, J = 15.6 Hz), 7.62 (d, 2H, J = 8.0 Hz), 7.55 (d, 2H, J = 6.8 Hz), 7.22 (d, 1H, J = 8.0 Hz), 7.07 (t, 1H, J = 8.0 Hz), 6.89 (m, 2H), 6.76 (t, 1H, J = 8.0 Hz), 4.35 (m, 1H, epimer A), 4.32 (m, 1H, epimer B), 3.86 (s, 1H, epimer A), 3.85 (s, 1H, epimer B), 3.75 (m, 1H), 3.15 (m, 1H, epimer A), 3.10 (m, 2H), 2.95 (m, 1H, epimer B), 2.70 (m, 1H), 2.60-2.30 (m, 6H), 2.18 (m, 1H), 1.92 (m, 3H), 1.70 (m, 3H). |
| 7-24 | $^1$H NMR (d$_4$-MeOD, 400 MHz) 7.68 (d, 1H, J = 15.6 Hz), 7.62 (d, 2H, J = 8.0 Hz), 7.55 (d, 2H, J = 8.4 Hz), 7.22 (d, 1H, J = 8.0 Hz), 7.07 (t, 1H, J = 8.0 Hz), 6.89 (m, 2H), 6.76 (t, 1H, J = 8.0 Hz), 4.35 (m, 1H, epimer A), 4.32 (m, 1H, epimer B), 3.95-3.80 (m, 3H), 3.45 (t, 2H, J = 12 Hz), 3.18 (m, 1H, epimer A), 2.95 (m, 1H, epimer B), 2.70-2.30 (m, 3H), 2.18 (m, 1H), 1.90-1.55 (m, 6H). |

TABLE 2-continued

| Example # | NMR data |
|---|---|
| 7-25 | $^1$H NMR (d$_4$-MeOD, 400 MHz) 7.68 (d, 1H, J = 15.6 Hz), 7.62 (d, 2H, J = 8.0 Hz), 7.55 (d, 2H, J = 6.8 Hz), 7.22 (d, 1H, J = 7.2 Hz), 7.07 (t, 1H, J = 7.2 Hz), 6.89 (m, 2H), 6.77 (t, 1H, J = 7.6 Hz), 4.35 (m, 1H, epimer A), 4.32 (m, 1H, epimer B), 3.85 (m, 1H), 3.65 (m, 1H), 3.95 (m, 1H, epimer A), 2.70 (m, 1H, epimer B), 2.65-2.10 (m, 5H), 1.80-1.60 (m, 5H), 1.40-1.15 (m, 5H). |
| 7-26 | $^1$H NMR (d$_4$-MeOD, 400 MHz) 7.75-7.61 (m, 7H), 7.25 (m, 3H), 7.07 (t, 1H, J = 7.2 Hz), 6.89 (m, 2H), 6.77 (t, 1H, J = 7.2 Hz), 4.40 (m, 1H, epimer A), 4.35 (m, 1H, epimer B), 4.10 (broad s, 1H), 3.18 (m, 1H, epimer A), 3.08 (m, 1H, epimer B), 2.85-2.45 (m, 3H), 2.20 (m, 1H), 1.85 (m, 1H). |
| 7-27 | $^1$H NMR (d$_4$-MeOD, 400 MHz) 7.79 (d, 2H, J = 8.4 Hz), 7.70-7.65 (m, 5H), 7.61 (d, 2H, J = 8.4 Hz), 7.22 (d, 1H, J = 7.6 Hz), 7.06 (t, 1H, J = 7.2 Hz), 6.89 (d, 1H, J = 15.2 Hz), 6.87 (d, 1H, J = 7.2 Hz), 6.76 (t, 1H, J = 7.6 Hz), 5.15 (m, 1H, racemic diastereomer A), 4.62 (m, 1H, racemic diastereomer B), 4.05 (m, 1H), 3.12-2.95 (m, 3H), 2.85-2.40 (m, 4H), 2.25 (m, 1H), 2.10 (m, 3H), 1.90 (m, 1H). |
| 7-28 | $^1$H NMR (d$_4$-MeOD, 400 MHz) 7.68 (d, 1H, J = 15.6 Hz), 7.64 (m, 4H), 7.54 (d, 2H, J = 8.8 Hz), 7.45 (d, 2H, J = 8.8 Hz), 7.21 (d, 1H, J = 7.2 Hz), 7.07 (t, 1H, J = 7.2 Hz), 6.88 (d, 1H, J = 15.6 Hz), 6.87 (d, 1H, J = 8.0 Hz), 6.76 (t, 1H, J = 8.0 Hz), 3.97 (s, 1H), 2.80 (m, 1H), 2.62-2.49 (m, 3H), 2.35 (m, 1H), 1.85 (m, 2H), 1.20 (m, 6H). |
| 7-29 | $^1$H NMR (d$_6$-DMSO, 400 MHz) 10.19 (s, 1H, racemic diastereomer A), 10.16 (s, 1H, racemic diastereomer B), 9.41 (s, 1H, racemic diastereomer A), 9.39 (s, 1H, racemic diastereomer B), 7.61 (m, 4H), 7.53 (d, 1H, J = 16.8 Hz), 7.48 (d, 2H, J = 8.4 Hz), 7.34 (d, 2H, J = 8.4 Hz), 6.90 (m, 2H), 6.75 (d, 1H, J = 7.2 Hz), 6.58 (t, 1H, J = 7.6 Hz), 6.55 (d, 1H, J = 16.8 Hz), 4.95 (broad s, 2H), 3.99 (s, 1H), 3.39 (m, 2H), 2.70-2.30 (m, 9H), 1.95 (m, 1H), 1.65 (m, 1H), 1.95 (broad m, 3H). |
| 7-30 | $^1$H NMR (d$_6$-DMSO, 400 MHz) 10.20 (s, 1H), 9.40 (s, 1H), 7.59 (m, 4H), 7.53 (d, 1H, J = 15.6 Hz), 7.47 (d, 2H, J = 8.4 Hz), 7.34 (d, 2H, J = 8.4 Hz), 6.90 (m, 2H), 6.75 (d, 1H, J = 7.6 Hz), 6.58 (t, 1H, J = 7.6 Hz), 6.55 (d, 1H, J = 15.6 Hz), 4.95 (broad s, 2H), 4.02 (s, 1H), 2.85-2.20 (m, 9H), 1.95 (m, 1H), 1.68 (m, 1H), 1.45 (m, 6H). |
| 7-31 | $^1$H NMR (d$_4$-MeOD, 400 MHz) 7.90 (m, 4H), 7.70-7.60 (m, 5H), 7.22 (dd, 1H, J = 8.0 Hz, 1.2 Hz), 7.06 (dt, 1H, J = 1.2 Hz, 8.0 Hz), 6.91-6.87 (m, 2H), 6.76 (dt, 1H, J = 1.2 Hz, 8.0 Hz), 4.07 (s, 1H, racemic diastereomer A), 4.06 (s, 1H, racemic diastereomer B), 3.52 (m, 1H), 3.10 (s, 3H), 2.88-2.50 (m, 8H), 2.13 (m, 1H), 1.87 (m, 1H), 1.10 (t, 6H, J = 7.2 Hz). |

Example 8

(2-Amino-phenyl)-carbamic acid tert-butyl ester

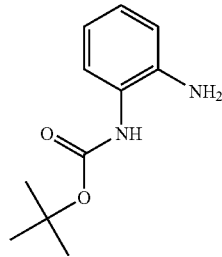

To a solution of o-phenylenediamine (54.0 g, 0.500 mol) in THF (500 mL) was added (Boc)$_2$O (109 g, 0.500 mol) in THF (150 mL) dropwise, and the mixture was stirred at room temperature overnight. After concentration under vacuum, the residue was diluted with ethyl acetate/petroleum ether=1/4 (v/v) (150 mL) and the precipitate was collected. The mother liquor was concentrated and the crude product was recrystallized with ethyl acetate/petroleum ether=1/4 (v/v). The combined solids were dried in vacuo at 40 degrees Celsius for 4 hours. An off-white solid (80 g, 77%) was obtained. MS: calc'd 209 (MH+), exp 209 (MH+). $^1$H NMR (CDCl$_3$, 400 MHz) δ 7.25 (m, 1H), 7.00 (m, 1H), 6.77 (m, 2H), 6.29 (broad m, 1H), 3.60 (broad m, 2H), 1.51 (s, 9H).

Example 9

(2-Acryloylamino-phenyl)-carbamic acid tert-butyl ester

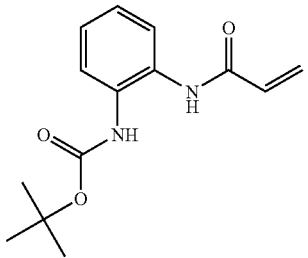

To a solution of acrylic acid (2.50 g, 34.7 mmol) in dichloromethane (80 mL) at 0 degrees Celsius was added N-methylmorpholine (4.73 g, 46.8 mmol), followed by isobutyl chloroformate (6.37 g, 46.8mmol). After 30 minutes, a solution of (2-amino-phenyl)-carbamic acid tertbutyl ester (5.80 g, 27.8 mmol) in dichloromethane (50 mL) was added dropwise to the refluxing reaction mixture over 30min. After the reaction was completed (2 hours later), the reaction mixture was allowed to cool down to room temperature, poured into ice water, and extracted with dichloromethane (30 mL×3). The organic layer was washed with water, dilute sodium bicarbonate solution, 0.1M HCl, water, and brine in turn. The organic layer was dried over sodium sulfate, filtered, and concentrated in vacuo. The crude solid was recrystallized from ethyl acetate/petroleum ether=1/4 (v/v) to obtain the desired product (2.5g, 34%). MS: calc'd 263 (MH+), exp 263 (MH+).

Example 10

(E)-{2-[3-(4-Formyl-phenyl)-acryloylamino]-phenyl}-carbamic acid tert-butyl ester

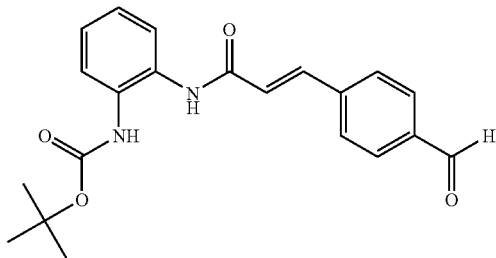

A mixture of (2-acryloylamino-phenyl)-carbamic acid tert-butyl ester (20.0 g, 76.3 mmol), 4-bromobenzaldehyde (14.4 g, 77.8 mmol), $Pd_2(dba)_3$ (0.56 g, 0.61 mmol), tri-o-tolyphosphine (0.370 g, 1.22 mmol) and triethylamine (42.1 mL, 0.300 mol) in DMF (300 mL) was stirred at 100 degrees Celsius under $N_2$ for 5 hours. The reaction mixture was allowed to cool down to room temperature and poured into a saturated aqueous solution of $NH_4Cl$. The precipitate was filtered off and washed with water, dried in vacuo at 40° C. overnight. The crude product was purified by flash column chromatography to obtain a yellow solid (15.5 g, 56%). MS: calc'd 367 (MH+), exp 367 (MH+). $^1H$ NMR ($d_6$-DMSO, 400 MHz) δ 10.0 (s, 1H), 9.79 (s, 1H), 8.53 (s, 1H), 7.98 (d, 2H, J=8.0 Hz), 7.87 (d, 2H, J=8.0 Hz), 7.68 (d, 1H, J=16 Hz), 7.60 (m, 2H), 7.14 (m, 2H), 7.10 (d, 1H, J =16 Hz), 1.46 (s, 9H).

Example 11

(E)-{4-[2-(2-tert-Butoxycarbonylamino-phenylcarbamoyl)-vinyl]-phenyl}-hydroxy-acetic acid methyl ester

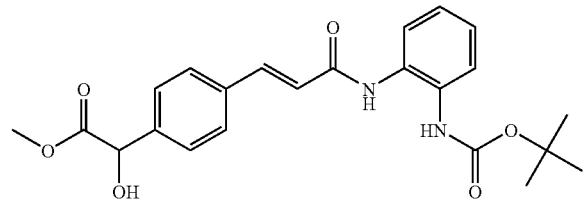

A mixture of 2-acryloylamino-phenyl)-carbamic acid tert-butyl ester (23 g, 87.7 mmol), methyl-2-(4-bromophenyl)-2-hydroxyacetate (25.6 g, 104.5 mmol), tri-o-tolyl-phosphine (2.8 g, 9.2 mmol), $Et_3N$ (35.8 g, 353.8 mmol) and $Pd_2(dba)_3$ (4.3 g, 4.7 mmol) in DMF (400 mL) was heated at 100 degrees Celsius for 6 hours under $N_2$ atmosphere, monitored by TLC. After cooling to room temperature, the mixture was poured into a saturated aqueous solution of $NH_4Cl$, and extracted with ethyl acetate. The organic layer was washed with brine, dried over $Na_2SO_4$, filtered, concentrated in vacuo, and purified by flash column chromatography (ethyl acetate/petroleum ether 1:2) to obtain pale yellow solid (22.4 g, 60%). MS: calc'd 427 (MH+), exp 427 (MH+). $^1H$ NMR ($d_6$-DMSO, 400 MHz) δ 9.71 (s, 1H), 8.48 (s, 1H), 7.64 (d, 2H, J=8.0 Hz), 7.59 (d, 1H, J=15.6 Hz), 7.57 (m, 1H), 7.48 (d, 2H, J=8.0 Hz), 7.14 (m, 2H), 6.92 (d, 1H, J=15.6), 6.17 (d, 1H, J=5.2 Hz), 5.21 (d, 1H, J =4.8 Hz), 3.64 (s, 3H), 1.47 (s, 9H).

Example 12

HDAC Inhibition by Novel Compounds: HeLa Extract HDAC Fluorometric Assay

Novel compounds were tested for their ability to inhibit histone deacetylase using an in vitro deacetylation assay. The enzyme source for this assay was HeLa nuclear extract. The substrate consisted of a commercial product containing an acetylated lysine side chain (both HeLa extract and substrate are available commercially from BIOMOL Research Laboratories, Inc., Plymouth Meeting, Pa.). After deacetylation of the substrate by incubation with HeLa nuclear extract, subsequent exposure to a developing reagent produces a fluorophore that is directly proportional to the level of deacetylation. Using the substrate concentration at the $K_m$ for the HeLa nuclear extract, the deacetylation assay was performed in the presence of novel compounds at 30 micromolar and the percent enzyme inhibition relative to a known reference HDAC inhibitor (SNDX-275) was determined. The compounds of the instant invention described in the Examples and Tables above exhibit histone deacetylase inhibitory activity in the range of about 95% to 180% relative to the known reference compound. Inhibitory activity for specific representative compounds can be found in Table 3.

Example 13 p21 Reporter Gene Induction By Novel Compounds

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37 degrees Celsius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng p21-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celsius in 5% $CO_2$, fresh media and test compounds were added to the wells and the cells further incubated for 15 hours at 37 degrees Celsius in 5% $CO_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit p21 induction activity in the range of about 2% to 300% relative to the known HDAC inhibitor (SNDX-275) at a concentration of 3 micromolar. Induction activity for specific representative compounds can be found in Table 3.

Example 14 gdf11 Reporter Gene Induction By Novel Compounds

The novel compounds of the present invention were tested for their ability to induce gdf11 (growth differentiation factor 11) gene expression using a reporter gene assay involving HeLa cells transfected with a gdf11 promoter-luciferase construct. The gdf11 promoter has been reported to be negatively regulated by HDAC3 (*Mol. Cell. Bio.* 2004, 24, 5106-5118). Briefly, the day before transfection, HeLa cells were seeded at 11,000 cells/well in a 96-well culture plate and incubated at 37 degrees Celsius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng gdf11-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celsius in 5% $CO_2$, fresh media and test compounds were added to the wells and the cells further incubated for 15 hours at 37 degrees Celsius in 5% $CO_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit gdf11 induction activity in the range of about 2% to 300% relative to the known HDAC inhibitor (SNDX-275) at a concentration of 3 micromolar. Induction activity for specific representative compounds can be found in Table 3.

Example 15 klf2 Reporter Gene Induction By Novel Compounds

The novel compounds of the present invention were tested for their ability to induce klf2 gene expression using a reporter gene assay involving A204 cells transfected with a klf2 promoter-luciferase construct. The klf2 promoter contained the MEF2 binding site for HDAC3/class IIa HDAC complex. Briefly, the day before transfection, A204 cells were seeded at 11,000 cells/well in a 96-well culture plate and incubated at 37 degrees Celsius in 5% $CO_2$ overnight. For transfection, the medium was removed and replaced with 100 microliters/well transfection media previously prepared as follows: 5 microliters serum-free DMEM, 0.15 microliters Fugene 6 reagent, 40 ng klf2-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celsius in 5% $CO_2$, fresh media and test compounds were added to the wells and the cells further incubated for 15 hours at 37 degrees Celsius in 5% $CO_2$. Finally, 10 ng/ml TNF-a was added and the cells further incubated for 4 hours. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit differential induction of p21 versus klf2 of 0.1 to 2.9-fold at 10 micromolar concentration. p21 versus klf2 selectivity for specific representative compounds can be found in Table 3.

Example 16

Antiproliferative Activity Against Cancer Cell Lines By Novel Compounds

The novel compounds of the present invention were tested for their ability to inhibit growth of various cancer cell lines using in vitro growth inhibition assays described below.

MTS Assay

Cells were seeded in 96-well culture plates (200 microliters/well at different seeding concentrations depending on cell type) and incubated overnight at 37 degrees Celsius in 5% $CO_2$. After adding compound dilutions to the cells (DMSO concentration kept below 0.5%), the cells were incubated at 37 degrees Celsius in 5% $CO_2$ for 72 hours. The effects on proliferation were determined by addition of MTS reagent (Promega) according to the manufacturer's instruction, followed by incubation for 2 hours at 37 degrees Celsius in 5% $CO_2$, and finally recording the absorbance at 490 nm using an ELISA plate reader.

WST Assay

Similar to MTS assay except that the developer is the CCK-8 reagent (Dojindo) and the plate reader is set to 450 nm absorbance.

The compounds of the instant invention described in the Examples and Tables above inhibited growth of cancer cell lines with 72 hour $GI_{50}$ values in the range of about 200 nanomolar to greater than 15 micromolar. $GI_{50}$ values against HT-29 colon cancer cells for specific representative compounds can be found in Table 3.

TABLE 3

| Example | HD (RP30) | p21 (RP3) | p21/klf2 (RP3) | p21/klf2 (RP10) | GI50 (micromolar) HT-29 |
|---|---|---|---|---|---|
| 7-16 | 159% | 157% | 0.7 | 0.9 | 0.2 |
| 7 | 163% | 187% | 0.8 | 1.2 | 0.4 |
| 7-17 | 164% | 163% | 0.7 | 1.0 | 0.7 |
| 7-7 | 183% | 230% | 2.1 | 2.0 | 2.3 |
| 7-6 | 175% | 216% | 2.3 | 2.9 | 3.0 |
| 7-29 | 144% | 293% | 1.2 | 1.4 | NA |
| 7-30 | 111% | 338% | 1.2 | 0.1 | 0.7 |

Table 3. Biological activity data for selected examples from the present invention. HDAC (RP30) is the relative inhibitory potency compared with SNDX-275 at 30 micromolar; p21 (RP3) is the relative induction potency compared with SNDX-275 at 3 micromolar; p21/klf2 (RP3) is the relative selectivity at 3 micromolar compared with SNDX-275 (p21/klf2 ratio defined as 1.0); p21/klf2 (RP10) is the relative selectivity at 10 micromolar compared with SNDX-275 (p21/klf2 ratio defined as 1.0).

The invention claimed is:
1. A compound according to formula (I),

(1)

wherein:
R¹ is selected from the group consisting of: hydrogen; lower alkyl; cycloalkyl; heterocyclyl; aryl and heteroaryl; wherein said lower alkyl; cycloalkyl; heterocyclyl; aryl or heteroaryl may be unsubstituted or once or several times substituted by: halogen; lower alkyl, which is unsubstituted or once or several times substituted by halogen; lower alkoxy; cycloalkyl; cyano; —NR$^a$R$^b$; —OCF$_3$; or —S(O)$_2$-lower alkyl;

R$^a$ and R$^b$ are:
each independently lower alkyl or cycloalkyl, or together with the nitrogen atom to which they are attached, form a 4 to 6 membered heterocyclyl;

R² and R³:
are each independently selected from the group consisting of: hydrogen; halogen; lower alkyl, which is unsubstituted or once substituted by hydroxy; lower alkoxy; hydroxy; heterocyclyl; —NRR'; or together with the carbon atoms to which they are attached, form a 4 to 6 membered cycloalkyl or a 4 to 6 membered heterocyclyl wherein one ring atom is a heteroatom;

R⁴ is selected from the group consisting of: hydrogen; halogen; lower alkyl, which is unsubstituted or once substituted by hydroxy; lower alkoxy; hydroxy; heterocyclyl; —NRR'; or R and R' are each independently selected from the group consisting of: hydrogen; lower alkyl substituted by hydroxy; —C(O)-lower alkyl; and lower alkyl; and
n is 0, 1 or 2;
or a pharmaceutically-active salt, racemic mixture, enantiomer, optical isomer, or tautomeric form thereof.

2. A compound according to claim 1, wherein
R¹ is phenyl or pyridinyl, said phenyl or pyridinyl unsubstituted or once or several times substituted by halogen; lower alkyl, which is unsubstituted or once or several times substituted by halogen; lower alkoxy; cycloalkyl; cyano; NR$^a$R$^b$; —OCF$_3$; or —S(O)$_2$-lower alkyl.

3. A compound according to claim 1, wherein
R¹ is phenyl, which is once or twice substituted by a substituent independently selected from the group consisting of: halogen; lower alkyl; —CF$_3$; cyclopropyl; cyano; —OCF$_3$; and —S(O)$_2$-lower alkyl;
R² and R³, together with the carbon atoms to which they are attached, form a 4 to 6 membered cycloalkyl or a 4 to 6 membered heterocyclyl wherein one ring atom is a heteroatom which is oxygen; or R² is selected from the group consisting of: hydrogen; hydroxy; methoxy; piperidinyl; pyrrolidinyl; and —NRR' and R³ is hydrogen; and
R⁴ is hydrogen.

4. A compound according to claim 1, wherein
R¹ is cycloalkyl or heterocyclyl.

5. A compound according to claim 1, wherein
R¹ is selected from the group consisting of: cyclopentyl, cyclohexyl, piperidinyl, and tetrahydro-pyran;
R² is hydroxy; and
R³ and R⁴ are each hydrogen.

6. A compound according to claim 1, selected from the group consisting of:
(E)-N-(2-Amino-phenyl)-3-{4-[(4-cyclopropyl-phenylcarbamoyl)-((S)-3-hydroxy-pyrrolidin-1-yl)-methyl]-phenyl}-acrylamide;
(E)-N-(2-Amino-phenyl)-3-{4-[(4-chloro-phenylcarbamoyl)-(3-diethylamino-pyrrolidin-1-yl)-methyl]-phenyl}-acrylamide;
(E)-N-(2-Amino-phenyl)-3-{4-[(4-bromo-phenylcarbamoyl)-((S)-3-hydroxy-pyrrolidin-1-yl)-methyl]-phenyl}-acrylamide;
(E)-N-(2-Amino-phenyl)-3-{4-[(4-bromo-phenylcarbamoyl)-((R)-3-hydroxy-pyrrolidin-1-yl)-methyl]-phenyl}-acrylamide;
(E)-N-(2-Amino-phenyl)-3-{4-[(1S,4S)-(4-bromo-phenylcarbamoyl)-2-oxa-5-aza-bicyclo[2.2.1]hept-5-yl-methyl]-phenyl}-acrylamide;
(E)-N-(2-Amino-phenyl)-3-{4-[((R)-3-dimethylamino-pyrrolidin-1-yl)-(4-trifluoromethyl-phenylcarbamoyl)-methyl]-phenyl}-acrylamide;
(E)-N-(2-Amino-phenyl)-3-{4-[(3-diethylamino-pyrrolidin-1-yl)-(4-trifluoromethyl-phenylcarbamoyl)-methyl]-phenyl}-acrylamide;
(E)-N-(2-Amino-phenyl)-3-{4-[((S)-3-hydroxy-pyrrolidin-1-yl)-(4-trifluoromethyl-phenylcarbamoyl)-methyl]-phenyl}-acrylamide;
(E)-N-(2-Amino-phenyl)-3-{4-[((S)-3-hydroxy-pyrrolidin-1-yl)-(4-isopropyl-phenylcarbamoyl)-methyl]-phenyl}-acrylamide; and
(E)-N-(2-Amino-phenyl)-3-{4-[(4-chloro-phenylcarbamoyl)-((S)-3-hydroxy-pyrrolidin-1-yl)-methyl]-phenyl}-acrylamide;
(E)-N-(2-Amino-phenyl)-3-{4-[(4-cyano-phenylcarbamoyl)-((S)-3-hydroxy-pyrrolidin-1-yl)-methyl]-phenyl}-acrylamide;
(E)-N-(2-Amino-phenyl)-3-{4-[(4-fluoro-phenylcarbamoyl)-((S)-3-hydroxy-pyrrolidin-1-yl)-methyl]-phenyl}-acrylamide;
(E)-N-(2-Amino-phenyl)-3-{4-[(3-diethylamino-pyrrolidin-1-yl)-(4-isopropyl-phenylcarbamoyl)-methyl]-phenyl}-acrylamide;

(E)-N-(2-Amino-phenyl)-3-{4-[(4-cyclopropyl-phenyl-carbamoyl)-(3-diethylamino-pyrrolidin-1-yl)-methyl]-phenyl}-acrylamide;

(E)-N-(2-Amino-phenyl)-3-{4-[(4-cyano-phenylcarbamoyl)-(3-diethylamino-pyrrolidin-1-yl)-methyl]-phenyl}-acrylamide;

(E)-N-(2-Amino-phenyl)-3-{4-[(3-diethylamino-pyrrolidin-1-yl)-(4-fluoro-phenylcarbamoyl)-methyl]-phenyl}-acrylamide;

(E)-N-(2-Amino-phenyl)-3-{4-[(4-bromo-phenylcarbamoyl)-(3-diethylamino-pyrrolidin-1-yl)-methyl]-phenyl}-acrylamide;

(E)-N-(2-Amino-phenyl)-3-{4-[(2-fluoro-4-trifluoromethyl-phenylcarbamoyl)-((S)-3- hydroxy-pyrrolidin-1-yl)-methyl]-phenyl}-acrylamide;

(E)-N-(2-Amino-phenyl)-3-{4-[((S)-3-hydroxy-pyrrolidin-1-yl)-(6-trifluoromethyl-pyridin-3-ylcarbamoyl)-methyl]-phenyl}-acrylamide;

(E)-N-(2-Amino-phenyl)-3-{4-[((S)-3-hydroxy-pyrrol id in-1-yl)-(4-trifluoromethoxy-phenylcarbamoyl)-methyl]-phenyl}-acrylamide;

(E)-3-{4-[[3-(Acetyl-methyl-amino)-pyrrolidin-1-yl]-(4-trifluoromethyl-phenylcarbamoyl)-methyl]-phenyl}-N-(2-amino-phenyl)-acrylamide;

(E)-N-(2-Amino-phenyl)-3-(4-{(4-bromo-phenylcarbamoyl)-[3-(1-hydroxy-1-methyl-ethyl)- pyrrolidin-1-yl]-methyl}-phenyl)-acrylamide;

(E)-N-(2-Amino-phenyl)-3-[4-((4-bromo-phenylcarbamoyl)-{3-[ethyl-(2-hydroxy-ethyl)-amino]-pyrrolidin-1-yl}-methyl)-phenyl]-acrylamide;

(E)-N-(2-Amino-phenyl)-3-{4-[(4-bromo-phenylcarbamoyl)-(3-piperidin-1-yl-pyrrolidin-1-yl)-methyl]-phenyl}-acrylamide; and (E)-N-(2-Amino-phenyl)-3-{4-[(3-diethylamino-pyrrolidin-1-yl)-(4-methanesulfonyl-phenylcarbamoyl)-methyl]-phenyl}-acrylamide.

7. A pharmaceutical composition comprising a compound according to claim 1 and a pharmaceutically acceptable adjuvant.

8. A process for the manufacture of a compound according to claim 1, wherein a compound of the formula

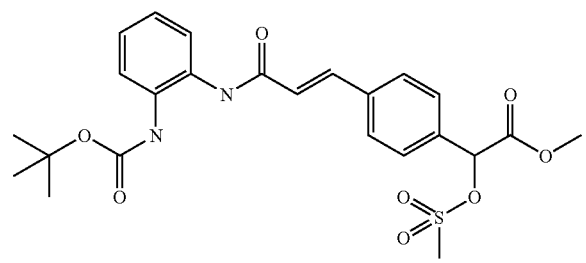

is reacted with a compound of the formula

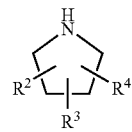

in the presence of TEA and DCM, to give a compound of the formula

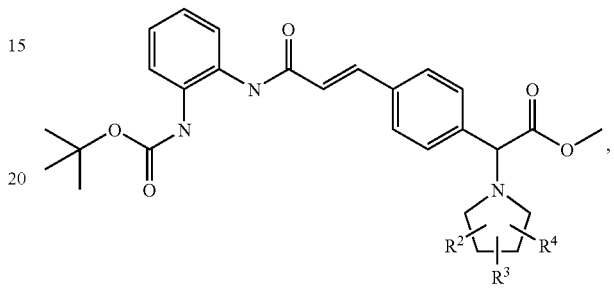

which is further reacted in the presence of LiOH and methanol to give the compound of formula

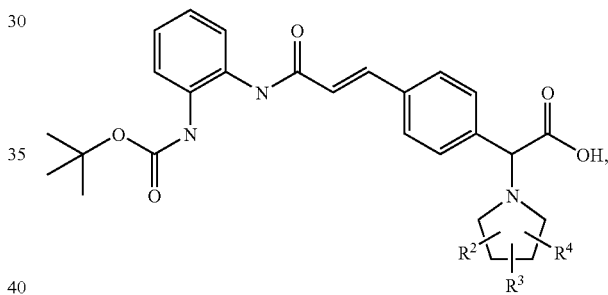

which is still further reacted in the presence of $R^1NH_2$ together with PyBroP, DIPEA and DCM to give the compound of formula

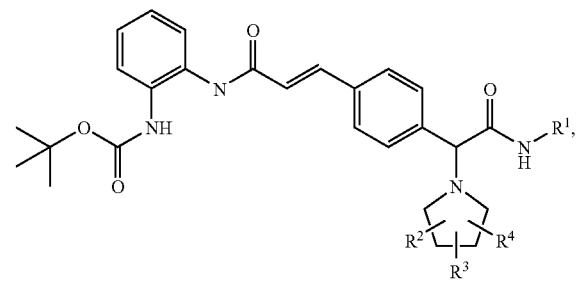

which is finally reacted in the presence of hydrochloric acid and methanol to give the compound of formula (I) according to claim 1, and wherein all substituent groups $R^1$, $R^2$, $R^3$ and $R^4$ have the meanings given in claim 1.

* * * * *

UNITED STATES PATENT AND TRADEMARK OFFICE
CERTIFICATE OF CORRECTION

PATENT NO. : 7,999,000 B2  Page 1 of 1
APPLICATION NO. : 12/463452
DATED : August 16, 2011
INVENTOR(S) : Wong et al.

It is certified that error appears in the above-identified patent and that said Letters Patent is hereby corrected as shown below:

Column 43, line 24, delete "-pyrrol id" and insert -- -pyrrolid- --.

Signed and Sealed this
Eleventh Day of October, 2011

David J. Kappos
*Director of the United States Patent and Trademark Office*